United States Patent
Carroll et al.

(10) Patent No.: US 9,150,581 B2
(45) Date of Patent: Oct. 6, 2015

(54) NICOTINIC RECEPTOR COMPOUNDS

(71) Applicants: RESEARCH TRIANGLE INSTITUTE, Research Triangle Park, NC (US); THE REGENTS OF THE UNIVERSITY OF MICHIGAN, Ann Arbor, MI (US); VIRGINIA COMMONWEALTH UNIVERSITY, Richmond, VA (US)

(72) Inventors: Frank Ivy Carroll, Durham, NC (US); Pauline Wanjiku Ondachi, Raleigh, NC (US); Hernan A. Navarro, Chapel Hill, NC (US); M. Imad Damaj, Richmond, VA (US); James H. Woods, Ann Arbor, MI (US); Emily M. Jutkiewicz, Ann Arbor, MI (US)

(73) Assignees: RESEARCH TRIANGLE INSTITUTE, Research Triangle Park, NC (US); THE REGENTS OF THE UNIVERSITY OF MICHIGAN, Ann Arbor, MI (US); VIRGINIA COMMONWEALTH UNIVERSITY, Richmond, VA (US)

( * ) Notice: Subject to any disclaimer, the term of this patent is extended or adjusted under 35 U.S.C. 154(b) by 0 days.

(21) Appl. No.: 14/368,111

(22) PCT Filed: Dec. 26, 2012

(86) PCT No.: PCT/US2012/071611
§ 371 (c)(1),
(2) Date: Jun. 23, 2014

(87) PCT Pub. No.: WO2013/101802
PCT Pub. Date: Jul. 4, 2013

(65) Prior Publication Data
US 2014/0357674 A1 Dec. 4, 2014

Related U.S. Application Data

(60) Provisional application No. 61/580,853, filed on Dec. 28, 2011.

(51) Int. Cl.
*C07D 487/08* (2006.01)
(52) U.S. Cl.
CPC .................................. *C07D 487/08* (2013.01)
(58) Field of Classification Search
CPC .................................................. C07D 487/08
See application file for complete search history.

(56) References Cited

U.S. PATENT DOCUMENTS 6,538,010 B1   3/2003   Carroll
7,615,567 B2  11/2009   Carroll

FOREIGN PATENT DOCUMENTS

WO          0237927 A2    5/2002
WO       2012024615 A1    2/2012

OTHER PUBLICATIONS

Patani et. al. "Bioisosterism: A Rational Approach in Drug Design" Chemical Reviews 1996, 96, 3147-3176.*
Wakefield, Basil "Fluorinated Pharmaceuticals" Innovations in Pharmaceutical Technology Jan. 2000, 74, 76-78, Online "http://www.iptonline.com/synopsis.asp?cat=5&article=1139/10/2010 11:41:03 AM".*
Abdrakhmanova, G., et al., "2-Fluoro-3-(4-nitrophenyl)deschloroepibatidine is a Novel Potent Competitive Antagonist of Human Neuronal alpha4beta2 nAChRs", "Molecular Pharmacology", 2006, pp. 1945-1952, vol. 69, No. 6.
Carroll, F., et al., "Synthesis, Nicotinic Acetylcholine Receptor Binding, and Antinociceptive Properties of 2-exo-2-(2'-Substituted-3'-phenyl-5'-pyridinyl)-7-azabicyclo[2.2.1]-heptanes. Novel Nicotinic Antagonist", "J. Med. Chem.", 2001, pp. 4039-4041, vol. 44.
Carroll, F., et al., "Synthesis, Nicotinic Acetylcholine Receptor Binding, and Antinociceptive Properties of 2-Fluoro-3-(substituted phenyl)deschloroepibatidine Analogues. Novel Nicotinic Antagonist", "J. Med. Chem.", 2004, pp. 4588-4594, vol. 47.
Carroll, F., et al., "Synthesis, Nicotinic Acetylcholine Receptor Binding, and Pharmacological Properties of 3-(Substituted phenyl) Deschloroepibatidine Analogs", "Bioorg Med Chem.", Jan. 15, 2008, pp. 746-754, vol. 16, No. 2.
Carroll, F., "Epibatidine Analogs Synthesized for Characterization of Nicotinic Pharmacophores—A Review", "Heterocycles", Oct. 23, 2008, pp. 99-120, vol. 79.
Huang, Y., et al., "Epibatidine analogues as selective ligands for the alphaxbeta2-containing subtypes of nicotinic acetylcholine receptors", "Bioorganic and Medicinal Chemistry Letters", 2005, pp. 4385-4388, vol. 15.
Jutkiewicz, E., et al., "Patterns of Nicotinic Receptor Antagonism: Nicotine Discrimination Studies", "The Journal of Pharmacology and Experimental Therapeutics", Oct. 2011, pp. 194-202, vol. 339, No. 1.

* cited by examiner

*Primary Examiner* — David K O Dell
(74) *Attorney, Agent, or Firm* — Hultquist, PLLC; Mary B. Grant

(57) ABSTRACT

Compounds and compositions for promoting smoking cessation or decreasing tobacco use or nicotine addiction are provided. The compounds are 2'-fluoro-3'-(substituted phenyl) deschloroepibatidine analogs. The compounds have been found to modulate neuronal nicotine acetylcholine receptors and are useful in methods for the treatment of conditions or disorders influenced by the modulation of neuronal nicotinic acetylcholine receptors.

20 Claims, 5 Drawing Sheets

NICOTINIC RECEPTOR COMPOUNDS

GOVERNMENT RIGHTS IN THE INVENTION

This invention was made with government support under Grant No. 2R01DA012001 awarded by the National Institutes of Health. The government has certain rights in the invention.

CROSS-REFERENCE TO RELATED APPLICATIONS

This application is a U.S. national phase under the provisions of 35 U.S.C. §371 of International Patent Application No. PCT/US12/71611 filed Dec. 26, 2012, which in turn claims priority of U.S. Provisional Patent Application No. 61/580,853 filed Dec. 28, 2011. The disclosures of such international patent application and U.S. priority provisional patent application are hereby incorporated herein by reference in their respective entireties, for all purposes.

FIELD

The present invention relates to methods, compounds and compositions for promoting smoking cessation or reducing tobacco use or combating nicotine addiction. The present invention further relates to methods, compounds and compositions for selectively modulating the function of a nicotinic acetylcholine receptor to provide pharmacotherapies capable of decreasing use of and combating addiction to tobacco products and of influencing other conditions or disorders affected by one or more of the nicotinic acetylcholine receptors.

DESCRIPTION OF THE RELATED ART

Smoking addiction is a complex phenomenon believed to involve cognition enhancement, psychological conditioning, stress adaptation, reinforcing properties and relief from withdrawal. Consequently, providing therapeutic treatment for smoking addiction is an extremely difficult challenge.

Tobacco products, including cigarettes, cigars, pipes and smokeless tobacco, can cause a variety of well-recognized health problems. From a public health perspective, it is desirable to minimize and ultimately eliminate the consumption of tobacco products, especially in the form of smoking. However, some individuals cannot quit smoking tobacco products, in spite of focused attempts to succeed. One major factor in the difficulty of quitting smoking is the presence of nicotine in tobacco. Nicotine can produce a myriad of behavioral effects and is unquestionably one of the most popular and powerful reinforcing agents. Both the psychological and physiological effects of tobacco smoke are attributed to a large extent to nicotine.

One method for assisting smoking cessation is to reduce consumption over time. For complex reasons, this method is not always entirely successful. A method for assisting smoking cessation is to provide an alternate delivery vehicle for nicotine. Such delivery vehicles include oral preparations such as chewing gums, and transdermal vehicles, such as skin patches.

Another method for assisting smoking cessation is to replace the nicotine signal from tobacco with a substitute reinforcer. Bupropion is used to promote smoking cessation and it may act as a substitute reinforcer.

Varenicline, a partial nicotine agonist, has been used for smoking cessation, but there is some evidence that varenicline produces increased risk of heart attack, stroke and/or other cardiovascular problems and neuropsychiatric side effects.

Nicotine antagonists also have been considered as an approach to smoking cessation. A nicotine antagonist would block the reinforcing signal from nicotine that creates and maintains the addiction to smoking. Over time, the smoker would dissociate the physical and psychological aspects of smoking. For example, the nonselective antagonist of nicotinic acetylcholine receptors mecamylamine has been used to promote smoking cessation; however, due to undesirable side effects, it is generally ineffective alone. Another approach is to administer an antagonist, e.g., mecamylamine, together with nicotine replacement therapy. Compounds which act as nicotine substitutes and block nicotine's effects would be preferred smoking cessation agents, but are difficult to identify.

Nicotinic acetylcholine receptors (nAChRs) are widely distributed throughout the central and peripheral nervous systems including several regions of the brain. These receptors are the body's targets for nicotine actions. Research suggests that $\alpha_4\beta_2$ nAChRs are the most abundant subtype in the brain and play a central role in nicotine addiction.

Epibatidine is a nicotinic agonist whose biological effects appear to be mediated by $\alpha_4\beta_2$ nAChRs. The high potency of epibatidine for $\alpha_4\beta_2$ nAChRs makes this agent a very useful lead compound for the development of new ligands for studying this nicotinic subtype. Such epibatidine analogs may be potent and/or selective for $\alpha_4\beta_2$ receptors and could provide a therapeutic treatment in addition to nicotine dependence, pain, and other neurological disorders. Some compounds related to epibatidine are described in U.S. Pat. No. 6,538,010, incorporated herein by reference in its entirety.

In spite of the known methods for treating smoking addiction, there remains a lack of generally effective means of treating and/or reducing smoking addiction. Accordingly, there remains a strong need for methods and agents for treating smoking addiction.

In consequence, the art continues to seek improvements in smoking cessation compounds, compositions and methods which may further be useful for other conditions or disorders involving the nicotinic acetylcholine receptors.

SUMMARY

The present disclosure relates to methods, compounds and compositions for promoting smoking cessation or reducing tobacco use or nicotine addiction. The present disclosure further relates to methods, compounds and compositions for selectively modulating the function of a nicotinic acetylcholine receptor to provide pharmacotherapies capable of decreasing use of and addiction to tobacco products and of influencing other conditions or disorders affected by one or more of the nicotinic acetylcholine receptors.

In one aspect, the disclosure relates to a compound according to formula I:

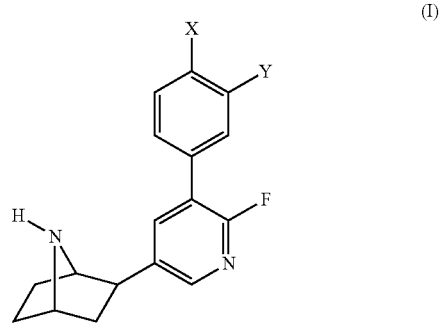

wherein X is H and Y is —SO₂CH₃, —SO₂NH₂, —SO₂CF₃, —CF₃, —CN, or —CONH₂; or X is —SO₂CH₃, —SO₂NH₂, —SO₂CF₃, —CF₃, —CN, or —CONH₂, and Y is H; or a pharmaceutically acceptable salt thereof.

In another aspect, the disclosure relates to a pharmaceutical composition comprising a compound of formula I and a pharmaceutically acceptable carrier.

In a further aspect, the disclosure relates to a method of treating nicotine addiction, comprising administering an effective amount of a compound according to formula I, or a composition comprising a compound according to formula I and a pharmaceutically acceptable carrier, to a subject in need thereof.

A further aspect of the disclosure relates to a method for selectively modulating the function of a nicotinic acetylcholine receptor comprising administering to a subject in need thereof an effective amount of a compound according to formula I or a composition comprising a compound according to formula I and a pharmaceutically acceptable carrier.

A still further aspect of the disclosure relates to a method for treating a subject having a condition or disorder for which modulation of nicotinic acetylcholine receptor activity is of therapeutic benefit, the method comprising administering to said subject having or susceptible to said condition or disorder an effective amount of a 2'-fluoro-3'-(substituted-phenyl)deschloroepibatidine analog compound demonstrating selective binding for a nicotinic acetylcholine receptor and exhibiting functional antagonist activity at a nicotinic acetylcholine receptor. In one aspect of the disclosure, the 2'-fluoro-3'-(substituted-phenyl)deschloroepibatidine analog compound demonstrates selective binding and functional antagonist activity at a nicotinic acetylcholine receptor which mediates at least one effect of nicotine. In a further aspect of this method, the 2'-fluoro-3'-(substituted-phenyl)deschloroepibatidineanalog compound is administered without interacting with nicotinic acetylcholine receptors that mediate cardiovascular changes. The compound may be a compound according to formula I. The method may further comprise administering to the subject an effective amount of a compound of formula I or a pharmaceutical composition comprising an effective amount of a compound of formula I and a pharmaceutically acceptable carrier.

A still further aspect of the disclosure relates to a method of attenuating discriminative stimulus effects of nicotine in a subject in need thereof, comprising administering to the subject an effective amount of a 2'-fluoro-3'-(substituted-phenyl)deschloroepibatidine analog compound which exhibits activity as a functional antagonist at a nicotinic acetylcholine receptor which mediates at least one effect of nicotine. In a further aspect, the 2'-fluoro-3'-(substituted-phenyl)deschloroepibatidine analog compound does not interact with nicotinic acetylcholine receptors that mediate cardiovascular changes. In another aspect, the method comprises administering to the subject an effective amount of a compound of formula I or a pharmaceutical composition comprising an effective amount of a compound of formula I and a pharmaceutically acceptable carrier.

Other aspects, features and embodiments of the disclosure will be more fully apparent from the ensuing description and appended claims.

DETAILED DESCRIPTION AND PREFERRED EMBODIMENTS

Figure 1:
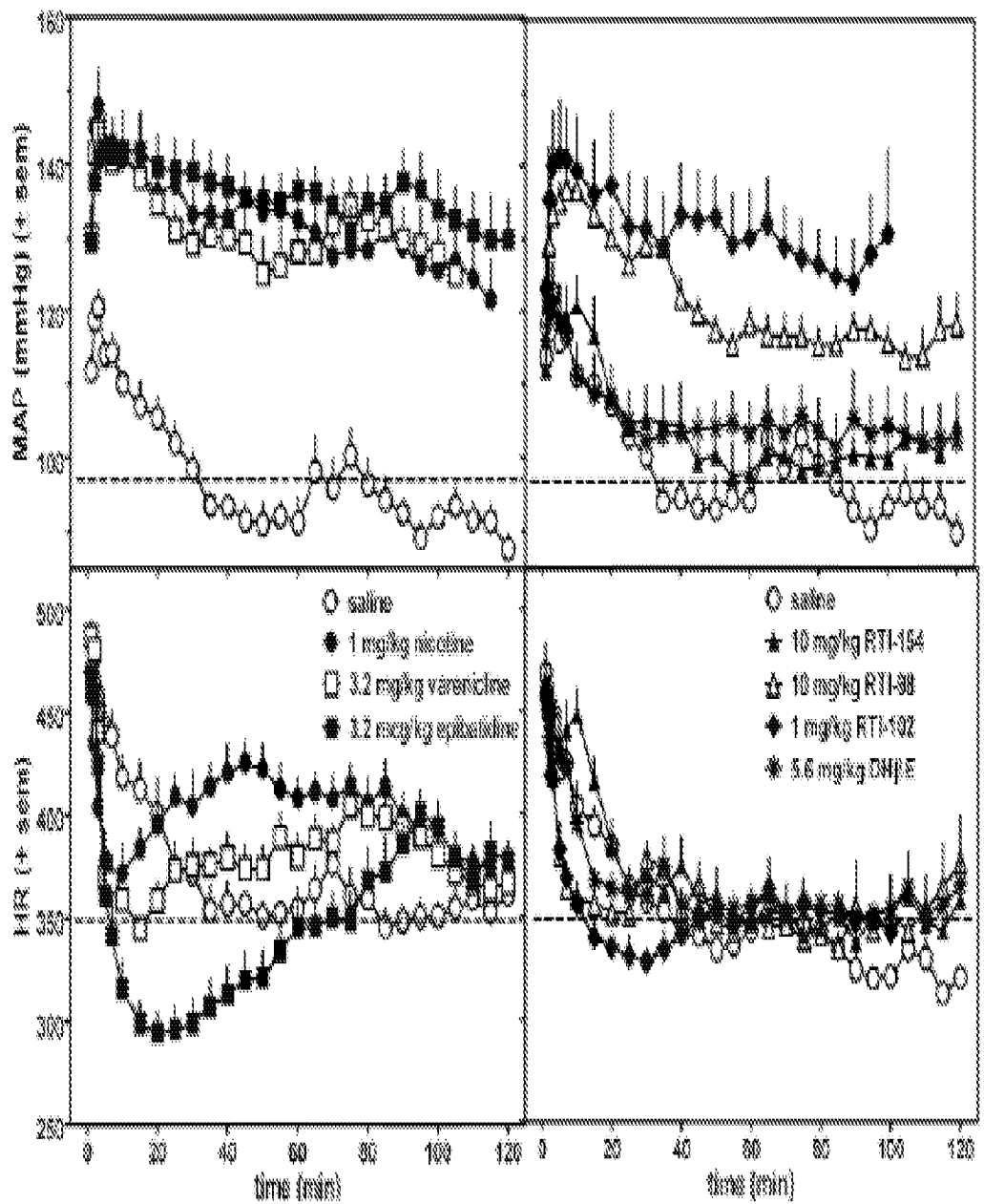
FIG. 1 is a graphical representation of cardiovascular effects mean arterial pressure and heart rate observed over time in rats after administration of saline, nicotine, varenicline, epibatidine, comparative compounds RTI-98 and RTI-102, and a compound according to the present disclosure, RTI-154.

The present disclosure relates to compounds, compositions and methods useful for promoting smoking cessation or reducing tobacco use or nicotine addiction. Such compounds mediate response by activity at one or more of the nicotinic acetylcholine receptors (nAChR).

In one aspect of the disclosure, a compound according to formula I is provided:

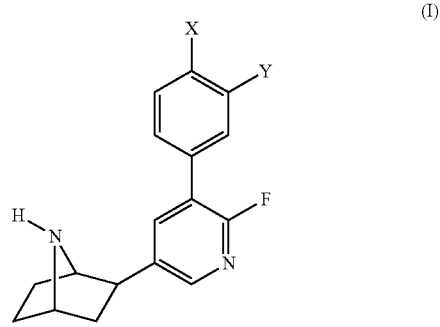

(I)

wherein X is H and Y is —SO₂CH₃, —SO₂NH₂, —SO₂CF₃, —CF₃, —CN, or —CONH₂; or X is —SO₂CH₃, —SO₂NH₂, —SO₂CF₃, —CF₃, —CN, or —CONH₂, and Y is H; or a pharmaceutically acceptable salt thereof. Pharmaceutical compositions comprising the compounds of formula I and a pharmaceutically acceptable carrier are provided.

The compounds of the disclosure are 2'-fluoro-3'-(substituted-phenyl)deschloroepibatidine analog compounds which include a strongly electron-withdrawing substituent X at the para-position or Y at the meta-position which has been found to provide improved properties over compounds previously used for smoking cessation. While not wishing to be bound by any theory or hypothesis as regards the specific mechanism of action of the compounds of the disclosure, such compounds appear to have functional antagonist activity at at least one of the nAChRs responsible for the effects of nicotine. By identifying compounds that are nicotine antagonists at appropriate nAChRs, pharmacotherapeutic compositions useful in smoking cessation, nicotine addiction and/or other conditions or disorders modulated by the nAChRs are provided.

Despite the proven efficacy of some current pharmacotherapies for tobacco dependence, relapse rates continue to be high. In addition to nicotine replacement therapy and the partial nicotinic agonist varenicline, the atypical antidepressant, bupropion, has exhibited some modest effectiveness in smoking cessation. However most of these drugs target nAChR subtypes, such as $\alpha_4\beta_2$ receptor subtype, with little selectivity. Nicotine is a non-selective nicotinic agonist, while varenicline is a partial $\alpha_4\beta_2$ receptor agonist but full agonist at $\alpha_3\beta_4$ and $\alpha_7$ receptor subtypes. Bupropion is a monoamine transporters inhibitor and a non-selective weak blocker of $\alpha_4\beta_2$ and $\alpha_3\beta_4$ nAChR subtypes.

In a specific aspect of the disclosure, the compounds of the disclosure have been found to act as nicotine antagonists at nAChRs involved in the effects of nicotine. More specifically, the compounds of the disclosure have been found to have high affinity for nAChRs responsible for the effects of nicotine, e.g., $\alpha_4\beta_2$ receptors, and have functional antagonistic activity at such nAChRs.

By targeting nicotinic acetylcholine receptors, it is believed that the described compounds will produce nAChR-mediated antagonism of nicotine discrimination, decrease both the reinforcing and motivational properties of nicotine and/or attenuate the decrease in brain reward function and increase in somatic signs associated with nicotine withdrawal. Thus, such compounds may be used in a method for selectively modulating the function of a nicotinic acetylcholine receptor, comprising administering to a subject, e.g., a human or mammalian subject, in need thereof an effective amount of a compound according to formula I. In one aspect of the disclosure, the selective modulation comprises inactivation of the function of one or more nicotinic acetylcholine receptor subtype as an antagonist. Such selective modulation in a particular aspect comprises inactivation of the function of nAChRs which are responsible for at least one of the effects of nicotine.

In the peripheral autonomic nervous system, nicotine activates nAChRs in both the sympathetic and parasympathetic ganglia and thereby has the capacity to increase or decrease heart rate and blood pressure. In addition, central nicotinic receptors in nuclei located primarily in the brainstem are also involved in cardiovascular control. Therefore, the cardiovascular effects of parenterally administered nicotine may be determined by multiple mechanisms of action.

The compounds of the disclosure are believed to provide improved properties for pharmacotherapeutic effects on conditions mediated by nAChRs. Compounds are desired that act as effective functional antagonists or, in some aspects, weak partial agonists, of nicotine's discriminative stimulus effects but have no negative cardiovascular effects due to an influence on the peripheral nAChRs. The compounds of the disclosure, thus, have nAChR antagonist activity which substantially blocks nicotine's discriminative stimulus effects without modifying the activity of acetylcholine on autonomic systems. In one aspect, the compounds are believed to not interact with nicotinic acetylcholine receptors that mediate cardiovascular changes.

Compounds with such receptor activity reduce nicotine discriminative stimulus and reinforcing effects and decrease the propensity for relapse to nicotine use. Such compounds may be used in a method of attenuating the discriminative stimulus effects of nicotine in a subject without producing cardiovascular changes. In one aspect, the method of attenuating the discriminative stimulus effects of nicotine comprises administering to the subject an effective amount of a compound which is a functional antagonist at a nicotinic acetylcholine receptor which mediates at least one effect of nicotine. In an additional aspect, the compound does not interact with nicotinic acetylcholine receptors that mediate cardiovascular changes.

The nicotinic acetylcholine receptor which mediates at least one effect of nicotine, in one aspect, is the $\alpha_4\beta_2$ receptor subtype.

Cardiovascular changes as used herein may include an increase in heart rate, an increase in blood pressure, increase in mean arterial pressure, or other cardiovascular changes known to occur upon activation of AChRs which affect the cardiovascular system.

In an aspect of the disclosure, the compound which is a functional antagonist at a nicotinic acetylcholine receptor which mediates at least one effect of nicotine, is a 2'-fluoro-3'-(substituted-phenyl)deschloroepibatidine analog compound. In another aspect, the compound is a compound according to formula I.

The compounds depicted as formula I are shown as a single enantiomeric compound; however, both enantiomers are within the scope of the present invention, such as in a racemic mixture. Moreover, it is within the specific scope of the present invention to administer compounds which are enantiomerically enriched in a single enantiomer. Within the context of the present invention enrichment in a single enantiomer may comprise an enantiomeric excess (e.e.) of ≥55%, even more preferably ≥70%, even more preferably ≥80%, even more preferably ≥90%, even more preferably ≥95%, even more preferably ≥98%.

An enantiomerically enriched composition may be prepared by conventional methods known to those of ordinary skill in the art, such as by using an enantiomerically enriched starting material or by resolution of a racemic mixture or a mixture of a lower enantiomeric purity. Resolution may be conducted by conventional methods known to those of skill in the art, such as by chiral chromatography, formation of diasteriomeric derivatives followed by separation, or enantioselective crystallization.

The compounds may be used in the form of a pharmaceutically acceptable salt via protonation of the amine with a pharmaceutically acceptable acid. The acid may be an inorganic acid or an organic acid. Suitable acids include, for example, hydrochloric, hydroiodic, hydrobromic, sulfuric, phosphoric, citric, acetic and formic acids.

A variety of administration techniques may be utilized, among them oral, transdermal or parenteral techniques such as subcutaneous, intravenous, intraperitoneal, intracerebral and intracerebroventricular injections, catheterizations and the like. Such methods of administration are well-known to those skilled in the art. For a general discussion of drug delivery systems and administration modalities, see Kirk-Othmer Encyclopedia of Chemical Technology, Fourth Edition, Volume 8, pp. 445-475.

Average quantities of the compounds may vary in accordance with the binding properties of the compound (i.e., affinity, onset and duration of binding) and in particular should be based upon the recommendations and prescription of a qualified physician.

The therapeutic compositions useful in practicing the therapeutic methods of this disclosure may include, in admixture, a pharmaceutically acceptable excipient (carrier) and one or more of the compounds of the invention, as described herein as an active ingredient.

The preparation of therapeutic compositions which contain such neuroactive compounds as active ingredients is well understood in the art. Such compositions may be prepared for oral administration, or as injectables, either as liquid solutions or suspensions, however, solid forms suitable for solution in, or suspension in, liquid prior to injection can also be prepared. The preparation can also be emulsified. The active therapeutic ingredient is often mixed with excipients which are pharmaceutically acceptable and compatible with the active ingredient. Suitable excipients are, for example, water, saline, dextrose, glycerol, ethanol, or the like and combinations thereof. In addition, if desired, the composition can contain minor amounts of auxiliary substances such as wetting or emulsifying agents, and pH buffering agents which enhance the effectiveness of the active ingredient. The compounds of the disclosure can be formulated into the therapeutic composition as neutralized pharmaceutically acceptable salt forms.

The therapeutic compositions are conventionally administered orally, by unit dose, for example. The term "unit dose" when used in reference to a therapeutic composition of the present invention refers to physically discrete units suitable as unitary dosage for humans, each unit containing a predetermined quantity of active material calculated to produce the desired therapeutic effect in association with the required diluent, i.e., carrier, or vehicle.

The compositions are administered in a manner compatible with the dosage formulation, and in an effective amount, typically an amount effective to obtain the desired effect, in one aspect, for example, a therapeutic effect. The quantity to be administered depends on the subject to be treated, the presence of other agonists and antagonists in the subject's system, and degree of binding or inhibition of binding desired. Precise amounts of active ingredient required to be administered depend on the judgment of the practitioner and are peculiar to each individual. However, suitable dosages may range from about 0.01 to about 1,000, preferably about 0.25 to about 500, and more preferably 10 to 50 milligrams of active ingredient per kilogram body weight of individual per day and depend on the route of administration. For oral administration, 1 to 100 milligrams of active ingredient per kilogram body weight of individual per day is a preferred dose. However, the exact dosage must be determined by factoring in rate of degradation in the stomach, absorption from the stomach, other medications administered, etc. Suitable regimes for administration are also variable, but are typified by an initial administration followed by repeated doses at one or more hour intervals by a subsequent injection or other administration. Alternatively, continuous intravenous infusion sufficient to maintain appropriate concentrations in the blood is contemplated.

The present disclosure provides a method of treating smoking addiction. This may be accomplished by administering a compound of the present disclosure to a patient in need of terminating a smoking addiction. While not wishing to bound by any particular theory, it is believed that smoking addiction may be successfully treated by blocking some of the pharmacological effects of nicotine, such as, but not limited to reinforcement, antinociception, hypothermia, drug discrimination and motor impairment, while also dissociating some of the reinforcing effects of smoking. Within the context of the present disclosure, a patient in need of terminating a smoking addiction is a person who smokes on a regular basis and is either unable or unwilling to terminate smoking on a regular basis. The method of treating a smoking addiction may be practiced by administering the compound of the present disclosure as described, preferably concurrently with or in advance of the act of smoking. In this fashion, the patient addicted to smoking will also be subject to the effects of the compounds while smoking, which can act to dissociate the reinforcing effects of smoking, from the act of smoking itself. The amount of the compound administered to be effective to dissociate the reinforcing effects of smoking from the act of smoking may vary depending on the patient and the nature of the patient's addiction to smoking; however, determination of effective dosages and treatment schedules is within the level of skill of those of ordinary skill in the art, without undue experimentation.

The present disclosure is also directed to a method of preventing an addiction to smoking, by administering a compound of the present disclosure. A person (patient) in need of preventing an addiction to smoking may be a non-smoker or an occasional smoker, who is concerned about developing an addiction to smoking. The method of preventing a smoking addiction may be practiced, by administering the compounds as described, preferably in advance of the act of smoking. In this fashion, subject to the effects of the compounds of the disclosure, the patient will not develop a strong association of the act of smoking with the reinforcing effects of smoking. The amount of compound administered to be effective to prevent the association of the reinforcing effects of smoking from the act of smoking may vary depending on the patient and the nature of the patient. However, determination of effective dosages and treatment schedules is within the level of skill of those of ordinary skill in the art, without undue experimentation.

The present disclosure is also directed to a method of treating nicotine addiction. This may be accomplished by administering a compound of the present disclosure to a patient in need thereof. Within the context of the present invention, a patient in need of terminating a nicotine addiction is a person who consumes nicotine on a regular basis and is either unable or unwilling to terminate nicotine consumption on a regular basis. The method of treating a nicotine addiction may be practiced, by administering compounds as described, preferably concurrent with or in advance of the act of nicotine consumption. In this fashion, the patient addicted to nicotine will also be subject to the effects of the compounds, which can act to dissociate the physiological effects of nicotine consumption from the act of consuming nicotine. The amount of compound administered to be effective to dissociate the physiological effects of nicotine from the act of nicotine consumption may vary depending on the patient and the nature of the patient's addiction to nicotine. However, determination of effective dosages and treatment schedules is within the level of skill of those of ordinary skill in the art, without undue experimentation.

The effectiveness of the present method is appreciated in the ability to block some but not all of the pharmacological effects of nicotine. In a preferred embodiment the present method blocks the pharmacological effects of antinociception, seizures, and motor impairment, while not affecting body temperature or drug discrimination.

According to another embodiment of the present disclosure, it is possible to prevent the development of an addiction to smoking, by administering to a subject in need of preventing an addiction to smoking, a compound according to the present disclosure. In this embodiment, the compound can be administered prophylactically in order to prevent a subject from becoming addicted to smoking in the first place. Alternatively, the compound can be administered to a subject who is in the process of smoking cessation in order to prevent a relapse.

According to another embodiment of the disclosure, it is possible to reduce the use of tobacco or nicotine containing products by administering to a subject in need of reducing their use of tobacco or nicotine containing products, a compound or pharmaceutical composition comprising said compound according to the present disclosure. The method of reducing the use of nicotine containing products may be practiced, by administering compounds as described, preferably concurrent with or in advance of the act of nicotine consumption. In this fashion, the subject or patient using such nicotine products will also be subject to the effects of the compounds, which can act to dissociate the physiological effects of nicotine consumption from the act of consuming nicotine. The amount of compound administered to be effective to dissociate the physiological effects of nicotine from the act of nicotine consumption may vary depending on the patient and the nature of the patient's addiction to nicotine. However, determination of effective dosages and treatment schedules is within the level of skill of those of ordinary skill in the art, without undue experimentation.

In another aspect of the disclosure, a method for treating a subject having a condition or disorder where modulation of nicotinic acetylcholine receptor activity is of therapeutic benefit is provided, the method comprising administering to said subject having or susceptible to said condition or disorder an effective amount of a compound demonstrating selective binding for a nicotinic acetylcholine receptor and exhibiting functional antagonist activity for a nicotinic acetylcholine receptor. The selective binding and functional antagonist activity may be exhibited e.g., at one type of nicotinic acetylcholine receptor or more than one type of nicotinic acetylcholine receptor. The method comprises the administration of the compound without effecting substantial cardiovascular changes such as, for example, an increase in heart rate, blood pressure, or mean arterial pressure. In one aspect of the disclosure, a method is provided for treating a subject having a condition or disorder where modulation of nicotinic acetylcholine receptor activity is of therapeutic benefit comprising administering to said subject having or susceptible to said condition or disorder an effective amount of a 2'-fluoro-3'-(substituted-phenyl)deschloroepibatidine analog compound demonstrating selective binding and functional antagonist activity at a nicotinic acetylcholine receptor which mediates at least one effect of nicotine, without interacting with nicotinic acetylcholine receptors that mediate cardiovascular changes.

In one aspect of this method, the compound is a 2'-fluoro-3'-(substituted-phenyl)deschloroepibatidine analog compound. Such method is applicable for patients addicted to smoking or nicotine or use of tobacco products, as well as other conditions or disorders for which modulation of a nicotinic acetylcholine receptor is of therapeutic benefit.

Examples of conditions or disorders, which conditions or disorders may include a variety of disease states, where modulation of nicotinic acetylcholine receptor activity is of therapeutic benefit may include Alzheimer's disease, Parkinson's disease, pain (e.g., analgesic activity), depression, Tourette's syndrome, inflammatory bowel syndrome, schizophrenia, anxiety, epilepsy, attention-deficit hyperactivity disorder, ulcerative colitis and obesity. 2'-fluoro-3'-(substituted-phenyl)deschloroepibatidine analog compounds, including the compounds of the disclosure, which demonstrate selective binding for nicotinic acetylcholine receptors, such as, for example, $\alpha_4\beta_2$ neuronal nicotinic receptor subtype, and exhibit functional antagonist activity for one or more nicotinic acetylcholine receptors, thus may be used to treat subjects with such conditions and disorders.

In one aspect of the disclosure, a method for selectively modulating the function of a nicotinic acetylcholine receptor where modulation of nicotinic acetylcholine receptor activity is of therapeutic benefit is provided comprising administering to a subject in need thereof an effective amount of a compound according to formula I or a composition comprising a compound according to formula I and a pharmaceutically acceptable carrier.

Thus, in addition to their use in smoking cessation as described above, the compounds of the present disclosure, by virtue of the function as nicotinic ligands, may be used to treat other disorders and conditions. The compounds of the present disclosure may be administered to a subject or patient in need thereof, e.g., a human, in an amount effective to treat these disorders or conditions.

As will be readily appreciated, the amount of compound administered to be effective for each disorder or condition, may vary depending on the patient and the nature of the patient's condition. However, determination of effective dosages and treatment schedules is within the level of skill of those of ordinary skill in the art, without undue experimentation. The dosage may range from 0.01 to 1000, preferably from about 0.25 to about 500 milligrams of the compound per kilogram of patient body weight per day, depending on the route of administration. The compounds may be administered as described above for smoking cessation. In embodiments, the compound is administered in a pharmaceutical composition comprising a compound according to Formula (I) and a pharmaceutically acceptable carrier.

In another aspect of the disclosure, a method of attenuating the discriminative stimulus effects of nicotine in a subject without producing cardiovascular changes is provided. The method comprises administering to the subject an effective amount of a compound which is a functional antagonist at nicotinic acetylcholine receptors. The lack of effect on the cardiovascular system is believed to be the result of selectively antagonizing the AChR's discriminatory stimulus effects without modifying the activity of acetylcholine on autonomic systems. A compound useful in this method comprises a 2'-fluoro-3'-(substituted-phenyl)deschloroepibatidine analog compound. In one aspect of this method, the compound which is a functional antagonist at one or more nAChRs, and is a compound according to formula I. In another aspect, the compound is administered in a pharmaceutical composition comprising a compound according to Formula (I) and a pharmaceutically acceptable carrier.

The advantages and features of the disclosure are further illustrated with reference to the following examples, which are not to be construed as in any way limiting the scope of the description but rather as illustrative of embodiments of the disclosure in specific synthesis and applications thereof.

EXAMPLES

Example 1

Synthesis of 2'-Fluoro-3'-(4-substituted-phenyl)deschloroepibatidine analogues

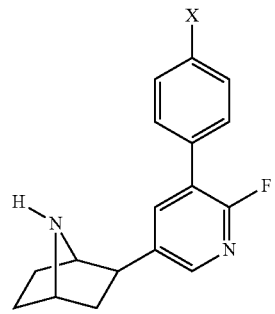

X=SO$_2$NH$_2$ (RTI-7527-192), SO$_2$CF$_3$ (RTI-7527-193), CF$_3$ (RTI-7527-153), SO$_2$CH$_3$ (RTI-7527-154), CN(RTI-7527-155)

The steps in the synthesis of 2'-fluoro-3'-(4-benzenesulfonamide), 2'-fluoro-3'-(4-trifluoromethanesulfonyl phenyl), 2'-fluoro-3'-(4-trifluoromethylphenyl), 2'-fluoro-3'-(4-methanesulfonylphenyl), and 2'-fluoro-3'-(4-cyanophenyl) deschloroepibatidines were carried out as represented in Schemes 1-4 below.

Heck-cross coupling of olefin 1, followed by bromination of 3 and fluorination of 4 via the Sandmeyer reactions were all performed to provide the 2'-fluoro-3'-bromo compound 5. Boc re-protection was achieved by stirring 5 in the presence of Boc anhydride, Et$_3$N and DMAP in THF as the solvent to furnish compound 6. Suzuki-Miyaura borylation of 2'-fluoro-3'-bromo deschloroepibatidine (6) was performed through a microwave assisted cross-coupling of 6 with bis(pinacolato) diboron in the presence of the weak base KOAc and PdCl$_2$dppf as catalyst, in anhydrous 1,4-dioxane, irradiated at 140° C. for 15 minutes to furnish the boronic ester 7 in 83% yield (Scheme 1). Compounds 6 and boronic ester 7 were used as the respective starting materials in the cross-coupling reactions that furnished the desired epibatidine analogues as shown in Schemes 2, 3 and 4 below.

Scheme 2.

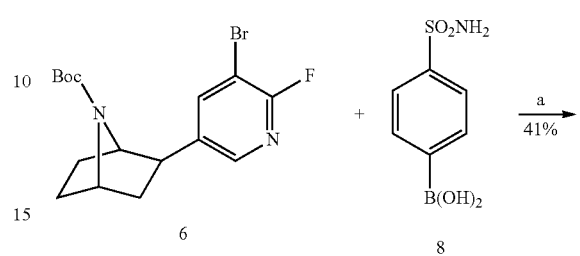

Scheme 1.

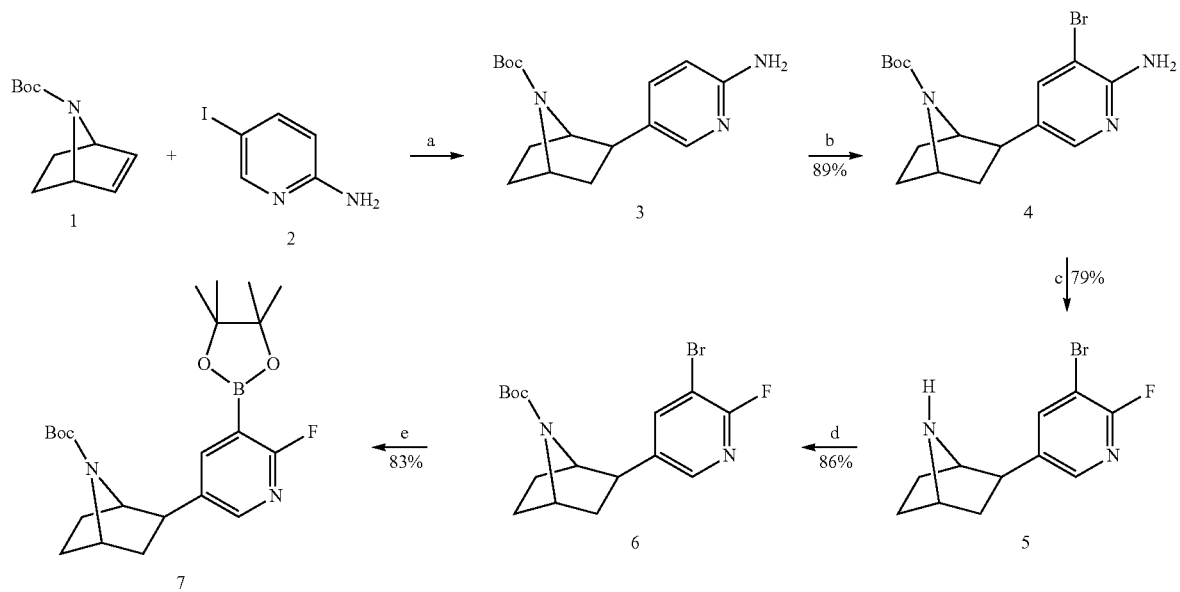

The reagents and conditions for Scheme 1 are: (a) Pd(OAc)$_2$, KO$_2$CH, (n-Bu)$_4$NCl, DMF, 100° C., 4 d; (b) Br$_2$, AcOH, NEt$_3$, CH$_2$Cl$_2$ 0° C. to rt overnight; (c) 70% HF-pyridine, NaNO$_2$ 0° C. to rt, 1 h; (d) Di-tert-butyl carbonate, THF, Et$_3$N, DMAP, 60° C. overnight; (e) Bis(pinacolato) diboron, KOAc, PdCl$_2$dppf, 1,4-dioxane, μw 140° C., 20 min.

A Suzuki cross-coupling of 6 was conducted with the commercially available 4-boronobenzene sulfonamide (8) through a microwave assisted reaction in the presence of PdCl$_2$dppf as catalyst, K$_2$CO$_3$ as base and 1,4-dioxane and water as solvents (Scheme 2). The reaction was irradiated at 140° C. for 20 mins to provide compound 9. Removal of the Boc protection by stirring 9 in TFA and CH$_2$Cl$_2$ for 2 hours furnished the amine 10 that was then converted to the HCl salt, compound RTI-7527-192.

-continued

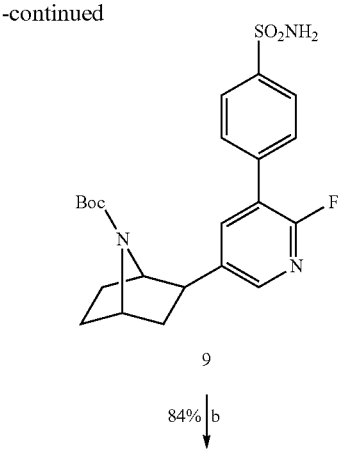

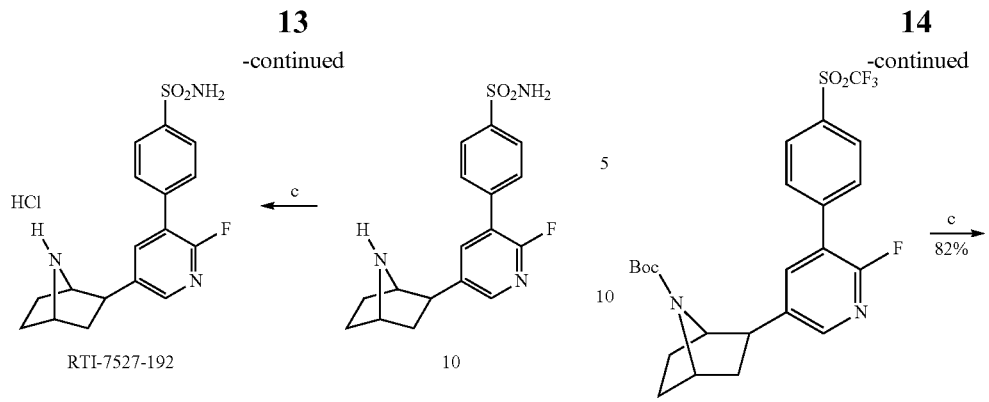

The reagents and conditions for Scheme 2 are: (a) PdCl$_2$dppf, K$_2$CO$_3$, 1,4-dioxane, H$_2$O, μw 140° C., 20 min.; (b) TFA, CH$_2$Cl$_2$, rt, 2 h; (c) HCl, Et$_2$O.

As illustrated in Scheme 3, the cross-coupling partner 4-bromophenyl(trifluoromethyl)sulfone (12) was prepared through oxidation of the commercially available 4-bromotrifluoromethylthiobenzene (11) with m-CPBA. Suzuki cross-coupling of 12 with the boronic ester 7 furnished compound 13 and subsequent removal of the Boc protection and conversion to the hydrochloride salt furnished RTI-7527-193.

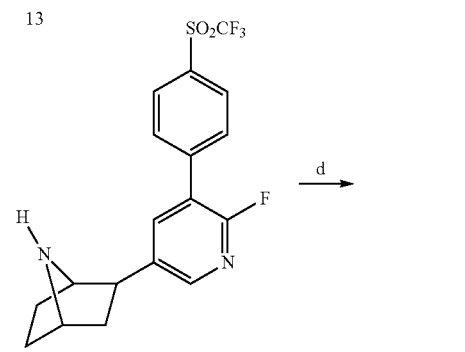

The reagents and conditions for scheme 3 are (a) m-CPBA, CH$_2$Cl$_2$, room temperature, overnight; (b) Pd(PPh$_3$)$_4$, K$_2$CO$_3$, DME-EtOH—H$_2$O, μw 140° C., 20 min; (c) TFA, CH$_2$Cl$_2$, room temperature, 2 h; (d) HCl, Et$_2$O.

Suzuki cross-coupling of 6 with 4-trifluoromethylphenyl-boronic acid, 4-methanesulphonylphenyl-boronic acid, and 4-cyanophenyl-boronic acid in the presence of palladium diacetate, tris(o-tolyl)phosphine, and sodium carbonate in a dimethoxyethane water mixture yielded compound 15, 16, and 17 (Scheme 4). Treatment of 15, 16, and 17 with trifluoroacetic acid in methylene chloride, followed by hydrochloride salt formation afforded RTI-7527-153, -154, and -155.

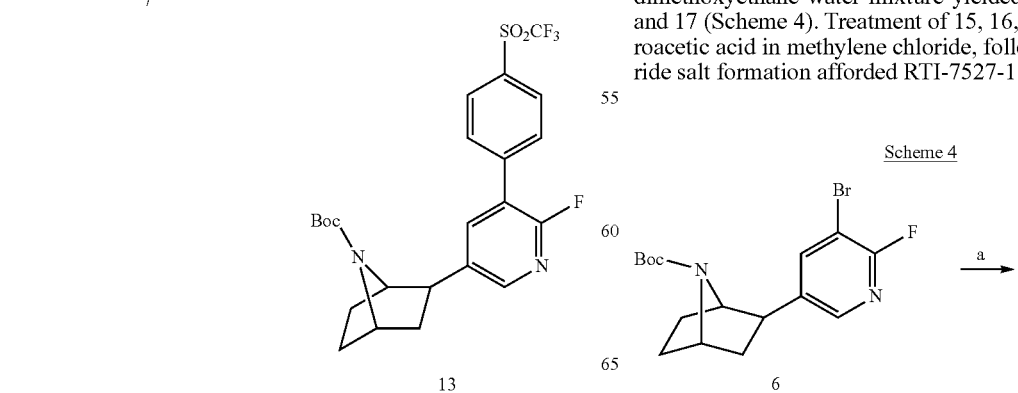

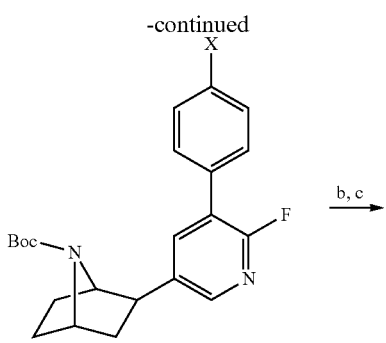

15. X = CF₃,
16. X = CN,
17. X = SO₂CH₃

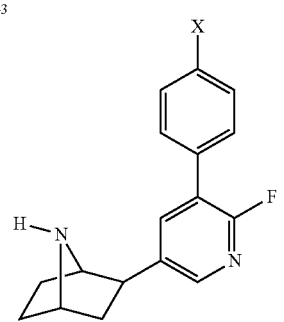

X = CF₃, RTI-7527-153
CN, RTI-7527-155
SO₂CH₃, RTI-7527-154

Reagents and Conditions: (a) Pd(OAc)₂, P(o-tolyl)₃, Na₂CO₃, DME, H₂O,

X—⟨benzene⟩—B(OH)₂ [X = CF₃, CN or SO₂CH₃]; (b) TFA, CH₂Cl₂;

(c) HCl (EtO), CH₃OH

Example 2
Experimental Procedures 7-tert-Butoxycarbonyl-2-exo-(2'-fluoro-3'-(4,4,5,5-tetramethyl-1,3,2-dioxaborolan-2-yl)-5'-pyridinyl)-7-azabicyclo[2.2.1]heptane (7)

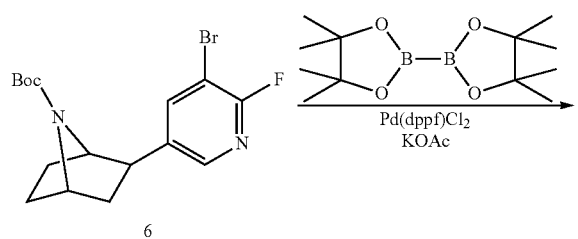

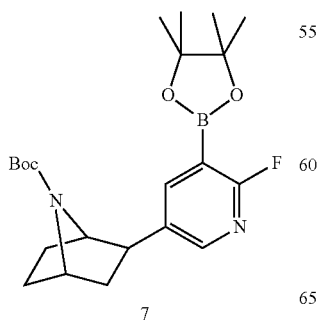

In a microwave vial was placed 7-tert-butoxycarbonyl-2-exo-(2'-fluoro-3'-bromo-5'-pyridinyl)-7-azabicyclo[2.2.1]heptane (6) (214 mg, 0.578 mmol, 1.0 equiv), bis(pinacolato)diboron (176 mg, 0.694 mmol, 1.2 equiv), KOAc (170 mg, 1.73 mmol, 3.0 equiv), Pd(dppf)Cl₂ (21 mg, 0.0289 mmol, 5 mol %) and anhydrous 1,4-dioxane (3 mL). The mixture was degassed through bubbling nitrogen for 20 min and then was irradiated in a microwave at 140° C. for 15 min. After cooling to room temperature, the mixture was diluted with EtOAc, filtered through a plug of Celite and anhydrous Na₂SO₄ and concentrated in vacuo. The resultant residue was purified by flash chromatograph through an ISCO column (EtOAc-hexanes) to provide 200 mg (83%) of 7 as a colorless oil.

$^{1}$H NMR (300 MHz, CDCl₃) δ (ppm) 1.26 (s, 12H), 1.44 (s, 9H), 1.60-1.53 (m, 2H), 1.75-1.92 (m, 3H), 1.96-2.03 (dd, J=9.0, 12.4 Hz, 1H), 2.87-2.92 (dd, J=4.8, 8.9 Hz, 1H), 4.19 (s, 1H), 4.40 (s, 1H), 8.07 (dd, J=8.4, 2.4 Hz, 1H), 8.17 (d, J=2.7 Hz, 1H); $^{13}$C NMR (75 MHz CDCl₃) δ (ppm) 24.80, 28.29 (3C), 28.77, 29.78, 40.20, 44.88, 61.80, 79.73, 84.31, 138.23 ($J_{CF}$=5.0 Hz), 146.8, 149.16 ($J_{CF}$=15.0 Hz), 154.89, 164.15, 167.36; MS (ESI) m/z 419.7 (M+H)⁺

7-tert-Butoxycarbonyl-2-exo-(2'-fluoro-3'-(4-benzene sulfonamide)-5'-pyridinyl)-7-azabicyclo[2.2.1]heptane (9)

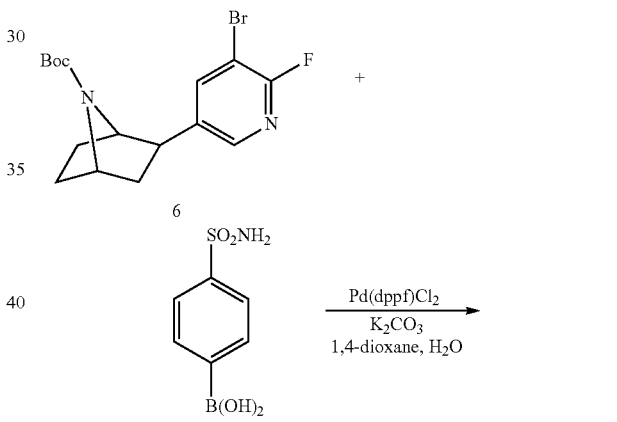

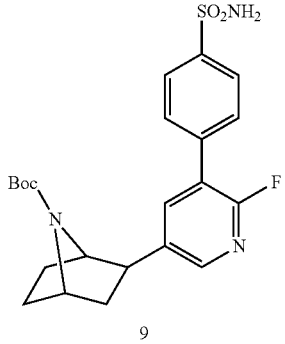

A solution of 6 (488 mg, 1.32 mmol), 4-boronobenzene-sulfonamide (8, 318 mg, 1.58 mmol), Pd(dppf)Cl₂ (48 mg, 0.066 mmol) and K₂CO₃ (547 mg, 3.96 mmol) in 1,4-dioxane (3 mL) and H₂O (1 mL) was placed in a microwave vial and degassed through bubbling nitrogen for 20 min. The reaction mixture was then irradiated in a CEM microwave reactor for 20 min at 140° C. After cooling to room temperature the mixture was diluted with 10 mL CHCl$_3$-MeOH (10:1) solution and then decanted into a 10 mL aqueous solution of NaHCO$_3$. The organic product was extracted with chloroform (3×20 mL) and the combined organic layers were dried over anhydrous Na$_2$SO$_4$, filtered through Celite and concentrated in vacuo. The resultant residue was purified by flash chromatography through an ISCO column to furnish 245 mg (41%) of 9 as a foamy compound.

$^1$H NMR (300 MHz, CDCl$_3$) δ (ppm) 1.41 (s, 9H), 1.53-1.66 (m, 2H), 1.81-1.93 (m, 3H), 1.98-2.09 (dd, J=9.0, 12.4 Hz, 1H), 2.95-3.00 (dd, J=4.8, 8.9 Hz, 1H), 4.24 (s, 1H), 4.40 (s, 1H), 5.47 (s, 2H), 7.67 (dd, J=1.4, 8.5 Hz, 2H), 7.91 (dd, J=9.6, 2.4 Hz, 1H), 7.98 (dd, J=1.9, 8.6 Hz, 2H), 8.10 (s, 1H); $^{13}$C NMR (75 MHz CDCl$_3$) δ (ppm) 28.26 (3C), 28.81, 29.63, 40.42, 44.69, 56.04, 61.94, 80.06, 121.39 ($J_{CF}$=28.2 Hz), 126.63, 129.37, 129.41, 138.17 ($J_{CF}$=5.2 Hz), 139.45 ($J_{CF}$=3.7 Hz), 139.97 ($J_{CF}$=4.8 Hz), 142.19 145.62, ($J_{CF}$=15.0 Hz), 155.03, 157.31, 160.49.

7-tert-Butoxycarbonyl-2-exo-(2'-fluoro-3'-(4-trifluoromethanesulfonyl-phenyl)-5'-pyridinyl)-7-azabicyclo[2.2.1]heptane (13)

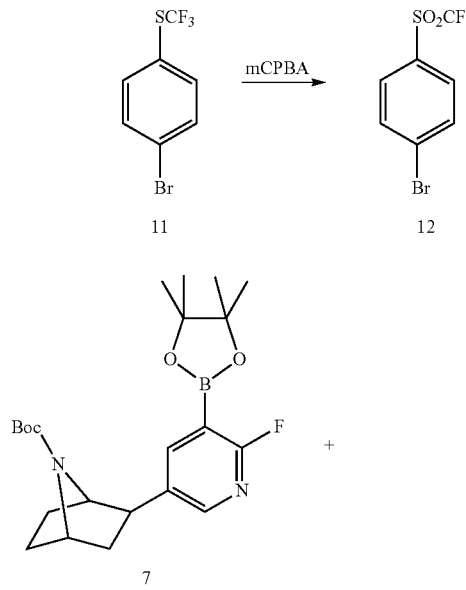

Preparation of 1-bromo-4-[(trifluoromethyl)sulfonyl]benzene (12): A stirred ice-cold solution of 4-bromophenyltrifluoromethylsulfide (11) (1.5 g, 5.83 mmol) in CH$_2$Cl$_2$ (40 mL) was treated with mCPBA (meta-chloroperoxybenzoic acid) (5.03 g, 29.2 mmol), and the reaction mixture was allowed to warm to room temperature. Stirring was continued overnight after which, the reaction mixture was diluted with additional CH$_2$Cl$_2$ (60 mL), washed sequentially with an aqueous saturated NaHCO$_3$ solution (50 mL) and brine (50 mL). The organic layer was dried over anhydrous MgSO$_4$, filtered through Celite and concentrated in vacuo to provide 1.12 g (67%) of 12 as a white crystalline solid that was used without further purification.

A solution of the boronic ester 7 (480 mg, 1.15 mmol), 12 (431 mg, 1.49 mmol), Pd(PPh$_3$)$_4$ (133 mg, 0.115 mmol) and K$_2$CO$_3$ (462 mg, 3.34 mmol) in DME-EtOH—H$_2$O (3.2 mL/0.8 mL/1 mL) was placed in a microwave vial and degassed through bubbling nitrogen for 20 min. The mixture was then irradiated in a CEM microwave reactor for 20 min at 140° C. After cooling to room temperature, the solvent was removed under reduced pressure and the residue was re-dissolved in CH$_2$Cl$_2$ (10 mL) and H$_2$O (10 mL) was added. The organic product was extracted with CH$_2$Cl$_2$ (3×20 mL), and the combined organic layers were dried over anhydrous Na$_2$SO$_4$, filtered through Celite and the solvent was removed in vacuo. The resultant residue was purified by flash chromatography through an ISCO column to furnish 408 mg (71%) of 13 as a colorless oil.

$^1$H NMR (300 MHz, CDCl$_3$) δ (ppm) 1.43 (s, 9H), 1.55-1.68 (m, 2H), 1.82-1.92 (m, 3H), 2.05-2.12 (dd, J=9.0, 12.4 Hz, 1H), 2.98-3.03 (dd, J=4.8, 8.9 Hz, 1H), 4.25 (s, 1H), 4.42 (s, 1H), 7.87 (d, J=8.3 Hz, 2H), 7.98 (dd, J=9.6, 2.6 Hz, 1H), 8.11 (d, J=8.4 Hz, 2H), 8.16 (s, 1H); $^{13}$C NMR (75 MHz CDCl$_3$) δ (ppm) 28.25 (3C), 28.81, 29.64, 40.69, 44.66, 55.98, 61.93, 79.99, 117.62, 120.59 ($J_{CF}$=28.3 Hz), 121.94, 130.16, 130.21, 130.85, 139.35 ($J_{CF}$=3.3 Hz), 140.23 ($J_{CF}$=4.9 Hz), 142.68 ($J_{CF}$=5.6 Hz), 146.75 ($J_{CF}$=15.0 Hz), 154.88, 157.29, 160.46.

General Procedure for removal of the Boc group from 9 and 13

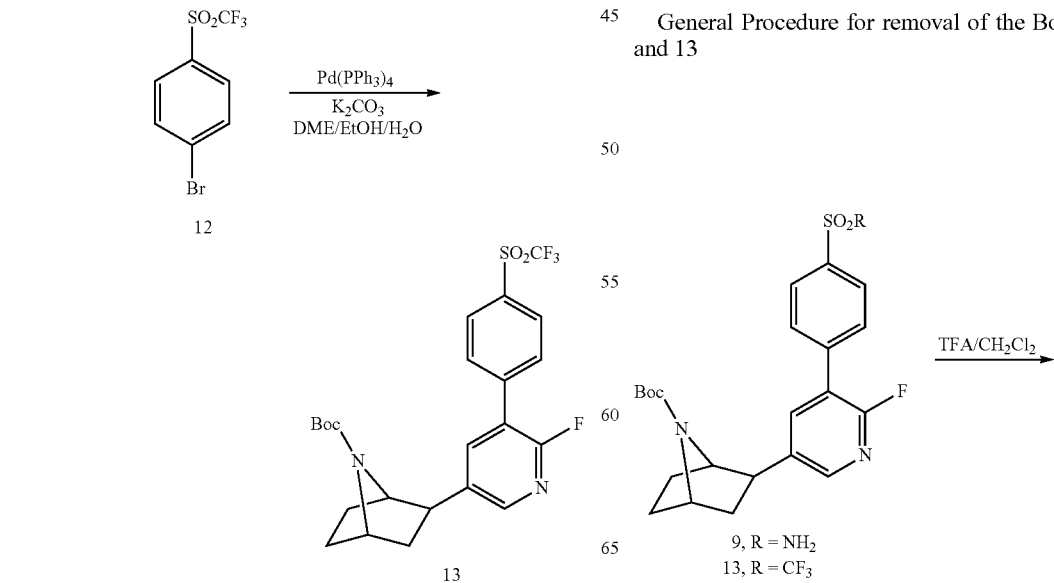

-continued

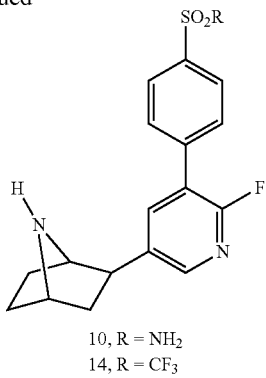

10, R = NH₂
14, R = CF₃

A solution of the Boc protected analog in CH₂Cl₂ (3 mL) and TFA (1 mL) was stirred at room temperature for 2 h. The solvent was removed under reduced pressure and the residual was treated with a 20 mL solution of NH₄OH—H₂O (3:1). The organic product was extracted with CHCl₃ (3×30 mL), dried over anhydrous sodium sulfate, filtered through Celite and concentrated in vacuo. Purification of the residual by flash chromatography through an ISCO column provided the amines 10 and 14 as colorless oils in 84% and 82% yields respectively.

Data for compound 10: $^1$H NMR (300 MHz, CD₃OD) δ (ppm) 1.48-1.80 (m, 5H), 2.02-2.09 (dd, J=9.1, 12.3 Hz, 1H), 3.02-3.07 (dd, J=4.8, 8.9 Hz, 1H), 3.67 (s, 1H), 3.76 (s, 1H), 7.78 (dd, J=1.5, 8.5 Hz, 2H), 7.91 (dd, J=8.6, 1.9 Hz, 2H), 8.06 (dd, J=2.4, 9.5 Hz, 1H), 8.14 (s, 1H); $^{13}$C NMR (75 MHz CD₃OD) δ (ppm) 29.90, 31.77, 41.04, 45.67, 57.85, 63.63, 104.59, 123.68 ($J_{CF}$=28.2 Hz), 127.50, 130.59, 130.63, 137.38 ($J_{CF}$=4.6 Hz), 141.52 ($J_{CF}$=3.1 Hz), 145.10, 146.70 ($J_{CF}$=14.6 Hz), 153.00, 157.61; MS (ESI) m/z 348.1 (M+H)$^+$ Data for compound 14: $^1$H NMR (300 MHz, CDCl₃) δ (ppm) 1.55-1.69 (m, 7H), 1.93-2.05 (dd, J=9.0, 12.4 Hz, 1H), 2.83-2.87 (dd, J=4.8, 8.9 Hz, 1H), 3.61 (s, 1H), 3.84 (s, 1H), 7.88 (dd, J=1.4, 8.5 Hz, 2H) 8.11-8.19 (m, 4H); $^{13}$C NMR (75 MHz CDCl₃) δ (ppm) 30.41, 31.56, 40.66, 44.25, 56.35, 62.94, 117.64, 120.39 ($J_{CF}$=28.2 Hz), 121.95, 130.21, 130.26, 131.01, 140.02 ($J_{CF}$=3.4 Hz), 141.45 ($J_{CF}$=4.7 Hz), 142.95 ($J_{CF}$=5.6 Hz), 146.80 ($J_{CF}$=14.7 Hz), 157.16, 160.33; MS (ESI) m/z 401.2 (M+H)$^+$ Amines 10 and 14 were converted to the respective hydrochloride salts using HCl in diethyl ether, to provide RTI-7527-192 and RTI-7527-193.

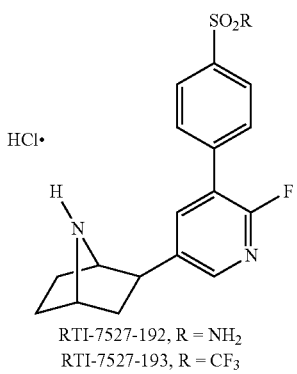

RTI-7527-192, R = NH₂
RTI-7527-193, R = CF₃

Data for RTI-7527-192: Mp. 205-208° C.; $^1$H NMR (300 MHz, METHANOL-d₄) δ (ppm) 1.87-2.19 (m, 5H), 2.45-2.53 (dd, J=9.6, 13.4 Hz, 1H), 3.51-3.56 (dd, J=4.8, 8.9 Hz, 1H), 4.33 (s, 1H), 4.55 (s, 1H), 7.81 (dd, J=1.5, 8.5 Hz, 2H), 8.01 (dd, J=1.8, 6.8 Hz, 2H), 8.09 (dd, J=2.4, 9.1 Hz, 1H), 8.22 (s, 1H); $^{13}$C NMR (75 MHz, METHANOL-d₄) δ (ppm) 27.00, 29.07, 37.78, 43.44, 60.37, 64.28, 103.00, 123.23, 127.56, 130.72, 130.76, 137.57, 138.69, 141.59, 145.07, 146.74 ($J_{CF}$=14.0 Hz), 159.00, 162.18; MS (ESI) m/z 348.1 [(M−HCl))$^+$, M=C₁₆H₁₈FN₃O₂S]; Anal. (C₁₇H₁₈FN₃O₂S.H₂O) C, H, N.

Data for RTI-7527-193: Mp. 144-148° C.; $^1$H NMR (300 MHz, METHANOL-d₄) δ (ppm) 1.85-2.22 (m, 5H), 2.47-2.54 (dd, J=9.6, 13.4 Hz, 1H), 3.53-3.58 (dd, J=4.8, 8.9 Hz, 1H), 4.35 (s, 1H), 4.61 (s, 1H), 8.07 (dd, J=1.4, 8.6 Hz, 2H) 8.16 (dd, J=2.4, 9.3 Hz, 1H), 8.21 (d, J=8.4 Hz, 2H), 8.29 (s, 1H); $^{13}$C NMR (75 MHz, METHANOL-d₄) δ (ppm) 26.82, 28.89, 37.59, 43.30, 60.50, 64.28, 119.13, 122.22 ($J_{CF}$=28.2 Hz), 123.44, 132.00, 132.28, 137.50, 141.80, 143.89 ($J_{CF}$=5.2 Hz), 147.89 ($J_{CF}$=14.8 Hz), 158.93, 162.11; MS (ESI) m/z 401.0 [(M−HCl))$^+$, M=C₁₈H₁₆F₄N₂O₂S]; Anal. (C₁₈H₁₆F₄N₂O₂S.H₂O) C, H, N.

2-(5-(4-Trifluoromethylphenyl)-6-fluoropyridin-3-yl)-7-azabicyclo[2.2.1]heptane-7-carboxylic acid tert-butyl ester (15)

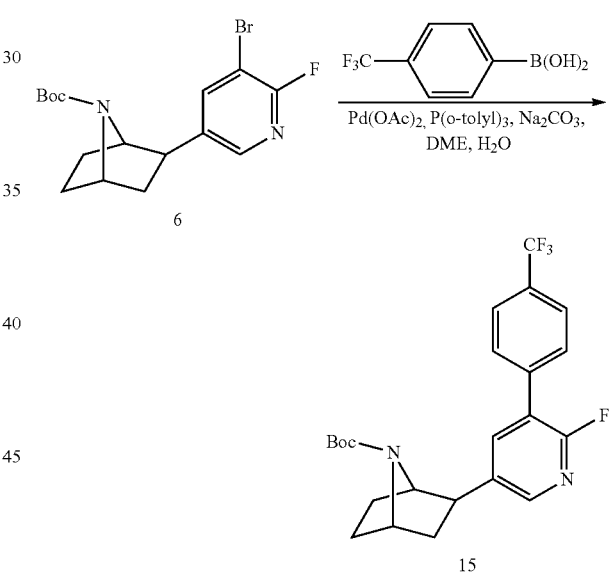

Compound 6 (259 mg, 0.7 mmol), 4-trifluoromethylphenylboronic acid (266 mg, 1.4 mmol), Pd(OAc)₂ (16 mg, 0.07 mmol), tris(o-tolyl)phosphine (43 mg, 0.14 mmol) and Na₂CO₃ (185 mg, 1.7 mmol) were mixed in DME (2 mL) and H₂O (0.5 mL). The mixture was purged with argon, sealed then heated in an 85° C. oil bath overnight. The mixture was cooled, then filtered through Celite and washed with EtOAc. The organic phase was washed with brine, dried over anhydrous Na₂SO₄ and concentrated. After flash chromatography on a silica gel column with EtOAc-hexanes, the title compound 15w as isolated as a clear oil (285 mg, 93%). $^1$H NMR (CDCl₃): δ (ppm) 1.43 (s, 9H), 1.5-1.9 (m, 5H), 2.02 (m, 1H), 2.98 (dd, 1H, J=4.8, 9.0 Hz), 4.25 (br s, 1H), 4.41 (br s, 1H), 7.70 (s, 4H), 7.91 (dd, 1H, J=2.4, 6.3 Hz), 8.10 (m, 1H). $^{13}$C NMR (CDCl₃): δ (ppm) 28.3, 28.9, 29.7, 40.7, 44.8, 56.1, 62.1, 80.0, 125.6 (q, J=15 Hz), 129.3 (d, J=12.6 Hz), 137.9 (d, J=18.6 Hz), 139.4 (d, J=15.3 Hz), 140.0 (d, J=19.5 Hz), 145.7 (d, J=58.2 Hz), 155.0, 157.5, 160.7.

2-(5-(4-Cyano-phenyl)-6-fluoro-pyridin-3-yl)-7-aza-bicyclo[2.2.1]heptane-7-carboxylic acid tert-butyl ester (16)

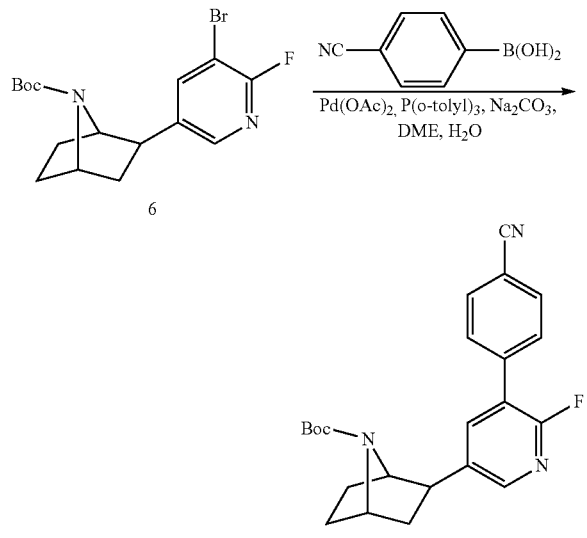

Compound 6 (259 mg, 0.7 mmol), 4-cyanophenylboronic acid (206 mg, 1.4 mmol), Pd(OAc)₂ (16 mg, 0.07 mmol), tris(o-tolyl)phosphine (43 mg, 0.14 mmol) and Na₂CO₃ (185 mg, 1.7 mmol) were mixed in DME (2 mL) and H₂O (0.5 mL). The mixture was purged with argon, sealed then heated in an 85° C. oil bath overnight. The reaction mixture was cooled, then filtered through Celite and washed with EtOAc. The organic phase was washed with brine, dried over anhydrous Na₂SO₄ and concentrated. After flash chromatography on a silica gel column with EtOAc-hexanes, the title compound 16w as isolated as a white solid (275 mg, 99%). $^1$H NMR (CDCl₃): δ (ppm) 1.43 (s, 9H), 1.5-1.9 (m, 5H), 2.02 (m, 1H), 2.99 (dd, 1H, J=4.8, 9.0 Hz), 4.25 (br s, 1H), 4.41 (br s, 1H), 7.6-7.8 (m, 4H), 7.92 (dd, 1H, J=2.4, 9.6 Hz), 8.12 (m, 1H). $^{13}$C NMR (CDCl₃): δ (ppm) 28.6, 29.2, 30.0, 41.0, 45.0, 56.3, 62.3, 80.3, 112.4, 116.7, 118.8, 121.7 (d, J=112.5 Hz), 129.8 (d, J=12.9 Hz), 132.7, 139.1, 139.5, 140.4, 146.5 (d, J=58.2 Hz), 155.3, 157.6, 160.8.

2-(5-(4-Methane sulphonyl-phenyl)-6-fluoro-pyridin-3-yl)-7-aza-bicyclo[2.2.1]heptane-7-carboxylic acid tert-butyl ester (17)

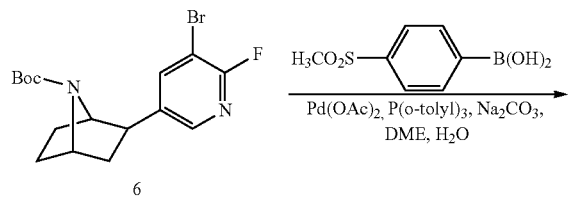

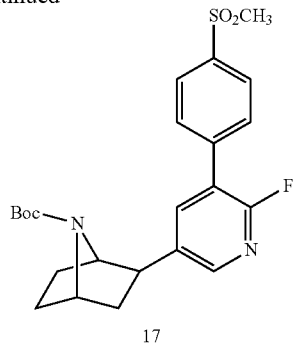

Compound 6 (259 mg, 0.7 mmol), 4-methanesulphonylphenylboronic acid (280 mg, 1.4 mmol), Pd(OAc)₂ (16 mg, 0.07 mmol), tris(o-tolyl)phosphine (43 mg, 0.14 mmol) and Na₂CO₃ (185 mg, 1.7 mmol) were mixed in DME (2 mL) and H₂O (0.5 mL). The reaction mixture was purged with argon, sealed then heated in an 85° C. oil bath overnight. The reaction mixture was cooled, then filtered through Celite and washed with EtOAc. The organic phase was washed with brine, dried over anhydrous Na₂SO₄ and concentrated. After flash chromatography on a silica gel column with EtOAc-hexanes, the title compound 17 was isolated as a white solid (312 mg, 99%). $^1$H NMR (CDCl₃): δ (ppm) 1.58 (s, 9H), 1.5-1.9 (m, 5H), 2.02 (m, 1H), 3.00 (dd, 1H, J=4.8, 9.0 Hz), 3.12 (s, 3H), 4.25 (br s, 1H), 4.41 (br s, 1H), 7.7-7.8 (m, 2H), 7.93 (dd, 1H, J=2.4, 9.6 Hz), 8.0-8.1 (m, 2H), 8.13 (m, 1H). $^{13}$C NMR (CDCl₃): δ (ppm) 28.6, 29.2, 30.0, 41.0, 44.9, 45.0, 56.4, 62.4, 80.3, 116.4, 121.8 (d, J=58.2 Hz), 128.1, 130.1 (d, J=13.2 Hz), 139.7, 140.0, 140.4, 146.5 (d, J=58.8 Hz), 155.4, 157.7, 160.9.

2-(5-(4-Trifluoromethane-phenyl)-6-fluoro-pyridin-3-yl)-7-aza-bicyclo[2.2.1]heptane

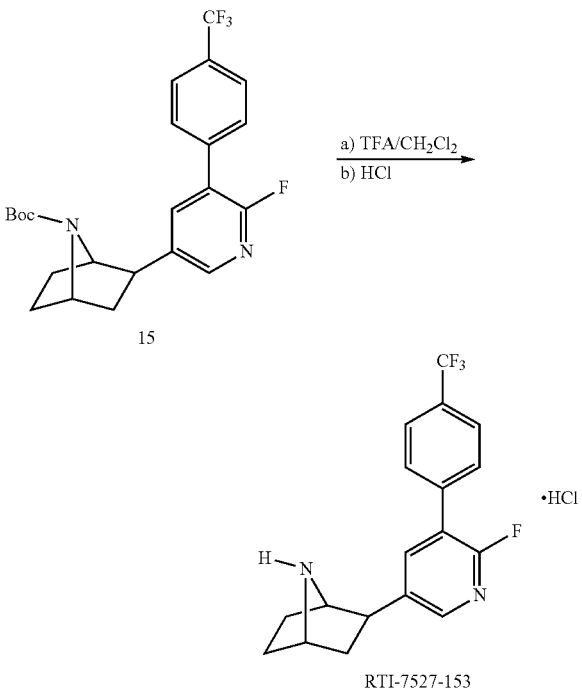

Compound 15 (285 mg, 0.65 mmol) was dissolved in anhydrous $CH_2Cl_2$ (3 mL) and cooled in an ice-water bath. TFA (3 mL) was added in 30 min. After stirring at room temperature for 1 hr, the mixture was poured into a cold solution of $NH_4OH$ in water (1:1). The mixture was then extracted with $CH_2Cl_2$. The organic phase was washed with brine, then dried over anhydrous $Na_2SO_4$ and evaporated to dryness. After flash chromatography on a silica gel column with $CH_2Cl_2$-MeOH, the free base was isolated as a clear oil (178 mg, 81%). $^1$H NMR ($CDCl_3$): δ (ppm) 1.5-1.7 (m, 5H), 1.8-1.9 (m, 1H), 2.83 (dd, 1H, J=5.1, 9.0 Hz), 3.62 (br s, 1H), 3.81 (br s, 1H), 7.70 (s, 4H), 8.06 (dd, 1H, J=2.4, 3.6 Hz), 8.13 (m, 1H). $^{13}$C NMR ($CDCl_3$): δ (ppm) 29.6, 30.6, 31.8, 40.9, 44.7, 56.8, 63.2, 125.9 (q, J=15 Hz), 129.6 (d, J=12.3 Hz), 140.2 (d, J=14.7 Hz), 141.4 (d, J=18.6 Hz), 146.1 (d, J=57.6 Hz), 157.7, 160.8, 162.7.

RTI-7527-153

2-(5-(4-Trifluoromethane-phenyl)-6-fluoro-pyridin-3-yl)-7-aza-bicyclo[2.2.1]heptane hydrochloride The free base (178 mg, 0.53 mmol) was dissolved in MeOH (5.3 mL) at room temperature. HCl (1M in ether, 5.3 mL) was added with a syringe pump over 50 min at room temperature. After stirring for 30 min, the solvent was removed. The residue was re-crystallized from MeOH-ether to give the title compound RTI-7527-153 as a yellow solid. Anal. ($C_{18}H_{17}ClF_4N_2.H_2O$): C, 55.32; H, 4.90; N, 7.17. found: C, 55.68; H, 4.99; N, 6.57.

2-(5-(4-Cyano-phenyl)-6-fluoro-pyridin-3-yl)-7-aza-bicyclo[2.2.1]heptane

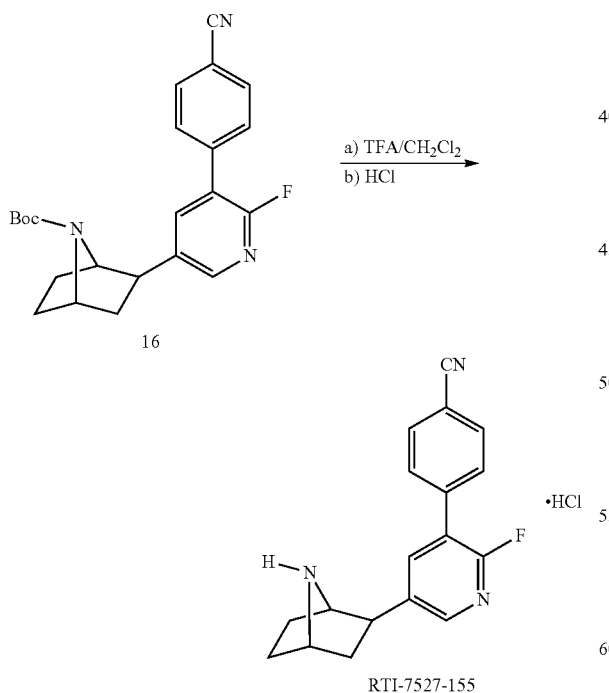

Compound 16 (275 mg, 0.7 mmol) was dissolved in anhydrous $CH_2Cl_2$ (3 mL) and cooled in an ice-water bath. TFA (3 mL) was added in 30 min. After stirring at room temperature for 1 hr, the mixture was poured into a cold solution of $NH_4OH$ in water (1:1). The mixture was then extracted with $CH_2Cl_2$. The organic phase was washed with brine then dried over anhydrous $Na_2SO_4$ and evaporated to dryness. After flash chromatography on a silica gel column with $CH_2Cl_2$-MeOH, the free base was isolated as a clear oil (200 mg, 93%). $^1$H NMR ($CDCl_3$): δ (ppm) 1.5-1.7 (m, 5H), 1.8-1.9 (m, 1H), 2.84 (dd, 1H, J=5.1, 9.0 Hz), 3.61 (br s, 1H), 3.82 (m, 1H), 7.6-7.8 (m, 4H), 8.09 (dd, 1H, J=2.4, 6.6 Hz), 8.14 (m, 1H). $^{13}$C NMR ($CDCl_3$): δ (ppm) 29.6, 30.7, 31.9, 40.9, 44.6, 56.8, 63.2, 112.3, 118.9, 121.5 (d, J=112.2 Hz), 129.9 (d, J=13.2 Hz), 132.7, 139.3, 140.1, 141.6, 146.5 (d, J=57.9 Hz), 157.5, 160.7.

RTI-7527-155

2-(5-(4-Cyano-phenyl)-6-fluoro-pyridin-3-yl)-7-aza-bicyclo[2.2.1]heptane hydrochloride The free base (200 mg, 0.68 mmol) was dissolved in MeOH (7 mL) at room temperature. HCl (1M in ether, 7 mL) was added with a syringe pump over 50 min at room temperature. After stirring for 30 min, the solvent was removed. The residue was re-crystallized from MeOH-ether to give the title compound as a yellow solid. Anal. ($C_{18}H_{17}ClFN_3.0.5H_2O$): C, 63.81; H, 5.35; N, 11.40. Found: C, 63.75; H, 5.70; N, 11.27.

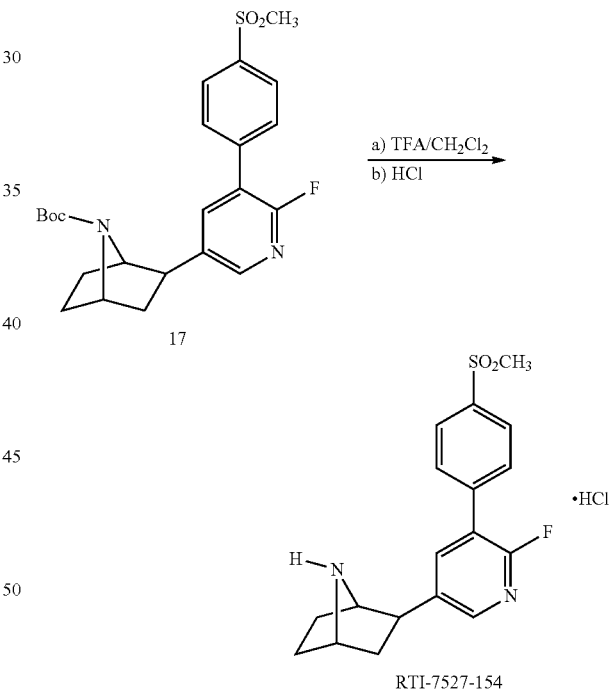

2-(5-(4-Methanesulphonyl-phenyl)-6-fluoro-pyridin-3-yl)-7-aza-bicyclo[2.2.1]heptane Compound 17 (312 mg, 0.7 mmol) was dissolved in anhydrous $CH_2Cl_2$ (3 mL) and cooled in an ice-water bath. TFA (3 mL) was added in 30 min. After stirring at room temperature for 1 hr, the mixture was poured into a cold solution of $NH_4OH$ in water (1:1). The mixture was then extracted with $CH_2Cl_2$. The organic phase was washed with brine, then dried over anhydrous $Na_2SO_4$ and evaporated to dryness. After flash chromatography on a silica gel column with $CH_2Cl_2$-

MeOH, the free base was isolated as a clear oil (242 mg, 99%). $^1$H NMR (CDCl$_3$): δ (ppm) 1.5-1.7 (m, 5H), 1.8-1.9 (m, 1H), 2.87 (dd, 1H, J=5.1, 9.0 Hz), 3.11 (s, 3H), 3.65 (br s, 1H), 3.84 (m, 1H), 7.7-7.8 (m, 2H), 8.0-8.05 (m, 2H), 8.09 (dd, 1H, J=2.4, 3.6 Hz), 8.15 (m, 1H). $^{13}$C NMR (CDCl$_3$): δ (ppm) 29.6, 30.5, 31.7, 40.8, 44.6, 44.9, 56.8, 63.2, 121.6 (d, J=112.5 Hz), 128.0, 130.2 (d, J=12.3 Hz), 140.3 (d, J=14.7 Hz), 141.3 (d, J=18.6 Hz), 146.6 (d, J=57.6 Hz), 157.6, 160.8. RTI-7527-154

2-(5-(4-Methanesulphonyl-phenyl)-6-fluoro-pyridin-3-yl)-7-aza-bicyclo[2.2.1]heptane hydrochloride The free base (242 mg, 0.7 mmol) was dissolved in MeOH (7 mL) at room temperature. HCl (1M in ether, 7 mL) was added with a syringe pump over 50 min at room temperature. After stirring for 30 min, the solvent was removed. The residue was re-crystallized from MeOH-ether to give the title compound RTI-7527-154 as a yellow solid. Anal. (C$_{18}$H$_{20}$ClFN$_2$O$_2$S.1.25H$_2$O): C, 53.33; H, 5.59; N, 6.91. found: C, 53.70; H, 5.66; N, 6.38.

Example 3

Synthesis of RTI-7527-168 and RTI-7257-169

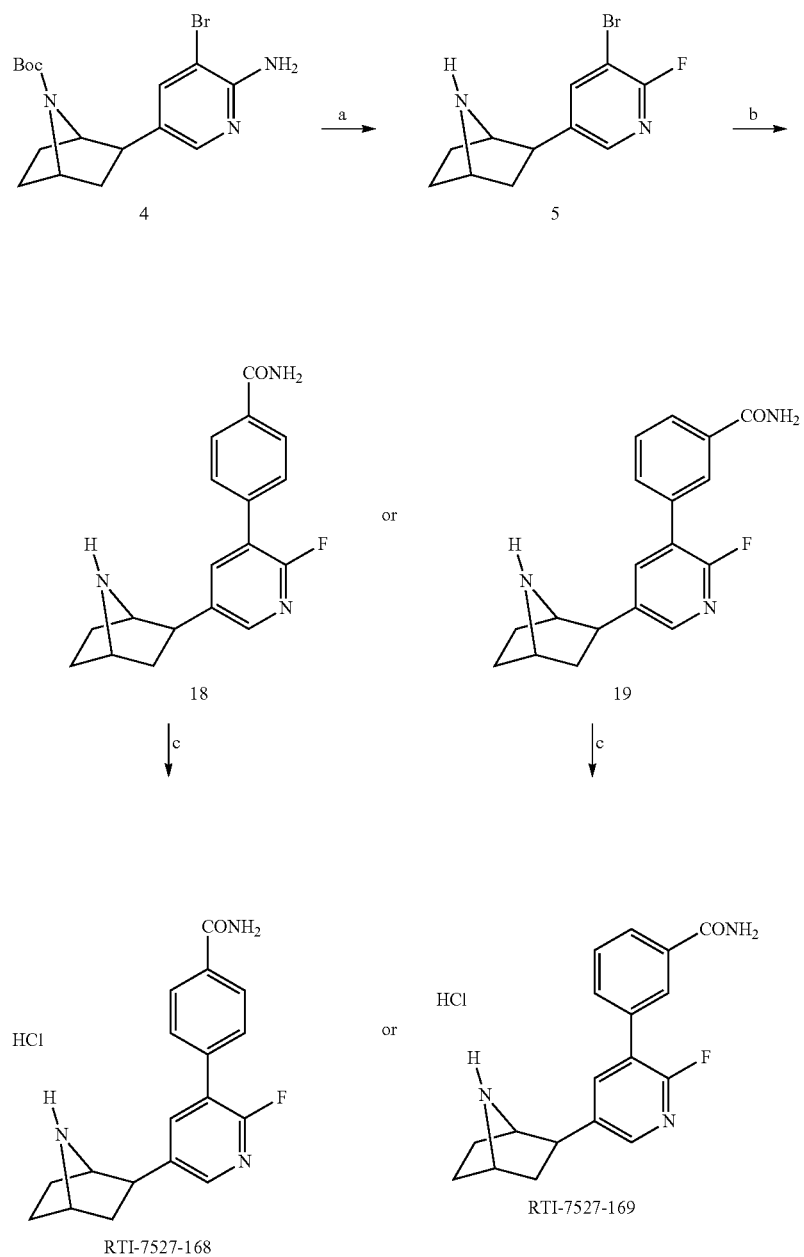

Scheme 5.

Reagents and conditions: (a) 70% HF-pyridine, NaNO$_2$ (b) Pd(PPh$_3$)$_4$, carbamoyl phenyl boronic acid, K$_2$CO$_3$, 1,4-dioxane, H$_2$O, reflux, 24 h (c) HCl in Ether.

2-exo-[2'-Fluoro-3'-(4-aminocarbonylphenyl)-5'-pyridinyl]-7-azabicyclo[2.2.1]heptane (18)

A solution of 2-exo-[2'-Fluoro-3'-bromo-5'-pyridinyl]-7-azabicyclo[2.2.1]heptane (5) (178 mg, 0.66 mmol), 4-carbamoylphenyl boronic acid (130 mg, 0.79 mmol), Pd(PPh$_3$)$_4$ (38 mg, 5 mol %), and K$_2$CO$_3$ (182 mg, 1.31 mmol) in 1,4-dioxane (5 mL) and H$_2$O (0.8 mL) in a sealed tube was degassed through bubbling N$_2$ for 20 min then heated at 100° C. for 20 h. After cooling to room temperature, the solvent was removed in vacuo and the residue was re-dissolved in EtOAc. Water (20 mL) was added and the organic product extracted with EtOAc (3×30 mL). The combined organic layers were dried over anhydrous MgSO$_4$, filtered through Celite and concentrated in vacuo. The crude residue was purified on silica gel (CHCl$_3$/MeOH) by flash chromatography to provide 160 mg, (78% yield) of the desired compound 18 as a colorless oil.

2-exo-[T-Fluoro-3'-(3-aminocarbonylphenyl)-5'-pyridinyl]-7-azabicyclo[2.2.1]heptane (19)

A solution of 5 (286 mg, 1.05 mmol), 3-carbamoylphenyl boronic acid (226 mg, 1.37 mmol), Pd(PPh$_3$)$_4$ (61 mg, 5 mol %), and K$_2$CO$_3$ (292 mg, 2.11 mmol) in 1,4-dioxane (5 mL) and H$_2$O (0.8 mL) in a sealed tube was degassed through bubbling N$_2$ for 20 min then heated at 100° C. for 20 h. After cooling to room temperature, the solvent was removed in vacuo and the residue was re-dissolved in EtOAc. Water (20 mL) was added and the organic product extracted with EtOAc (3×30 mL). The combined organic layers were dried over anhydrous MgSO$_4$, filtered through Celite and concentrated in vacuo. The crude residue was purified on silica gel (CHCl$_3$/MeOH) by flash chromatography to provide 258 mg, (79% yield) of the compound 19 as a colorless oil.

Data for Compound 18: 2-exo-[2'-Fluoro-3'-(4-aminocarbonylphenyl)-5'-pyridinyl]-7-azabicyclo[2.2.1]heptane $^1$H NMR (300 MHz, CDCl$_3$) δ 1.53-1.72 (m, 5H), 1.91-1.98 (m, 3H), 2.82-2.86 (m, 1H), 3.61 (s, 1H), 3.80 (s, 1H), 6.58 (br s, 2H), 7.62-7.65 (m, 2H), 7.89-7.92 (m, 2H), 8.01 (dd, J=2.4, 9.6 Hz, 1H), 8.10 (s, 1H); $^{13}$C NMR (CDCl$_3$) δ 30.2, 40.5, 44.4, 56.4, 62.8, 122.2, 127.1, 129.0, 133.1, 137.8, 139.8, 140.8, 145.6, 160.5, 169.1; MS (ESI) m/z 312.6 (M+H)$^+$.

Data for Compound 19: 2-exo-[2'-Fluoro-3'-(3-aminocarbonylphenyl)-5'-pyridinyl]-7-azabicyclo[2.2.1]heptane $^1$H NMR (300 MHz, CD$_3$OD) δ 1.46-1.74 (m, 5H), 1.99-2.03 (m, 1H), 2.95-3.00 (m, 1H), 3.62 (s, 1H), 3.74 (s, 1H), 7.54 (t, J=7.8 Hz 1H), 7.77 (dt, J=1.2, 7.8 Hz, 1H), 7.91 (dt, J=1.1, 7.8 Hz, 1H), 8.01 (dd, J=2.3, 9.6 Hz, 1H), 8.06 (s, 1H), 8.11 (s, 1H); $^{13}$C NMR (CD$_3$OD) δ 29.9, 31.8, 41.1, 45.7, 57.8, 63.7, 123.6, 128.7, 129.2, 130.0, 133.3, 132.9, 135.6, 141.4, 146.3, 158.6, 161.8, 171.7; MS (ESI) m/z 312.6 (M+H)$^+$.

Hydrochloride Salt Formation

A solution of the 18 or 19 in chloroform in a vial was treated with a solution of HCl in diethyl ether. The excess solvent was removed in vacuo and the salt dried under vacuum.

Data for RTI-7527-168 as a HCl Salt 2-exo-2-Fluoro-3-(4'-benzamide)deschloroepibatidine Hydrochloride. Obtained as a white solid in 99% yield. M.p. 202-206° C. $^1$H NMR (300 MHz, CD$_3$OD) δ 1.91-2.20 (m, 5H), 2.46-2.54 (dd, J=3.8, 9.6 Hz, 1H), 3.51-3.56 (m, 1H), 4.35, (d, J=3.5 Hz, 1H), 4.60 (d, J=2.5 Hz, 1H), 7.77-7.74 (m, 2H), 7.99-8.02 (m, 2H), 8.10 (dd, J=2.4, 9.2 Hz, 1H), 8.20 (s, 1H); $^{13}$C NMR (CD$_3$OD) δ 26.8, 28.9, 37.6, 43.3, 60.5, 64.3, 123.8, 129.1, 130.2, 135.0, 137.2, 138.3, 141.4, 146.4, 159.1, 162.3, 171.6; MS (ESI) m/z 312.4 (M+H)$^+$; Anal. (C$_{18}$H$_{19}$ClFN$_3$O.1.75 H$_2$O) C, H, N.

Data for RTI-7527-169 as a HCl Salt 2-exo-2-Fluoro-3-(3'-benzamide)deschloroepibatidine Hydrochloride. Obtained in a 99% yield as a white solid. $^1$H NMR (300 MHz, CD$_3$OD) δ 1.99-2.24 (m, 5H), 2.45-2.53 (dd, J=3.8, 9.6 Hz, 1H), 3.51-3.56 (m, 1H), 4.36, (d, J=3.5 Hz, 1H), 4.60 (d, J=2.5 Hz, 1H), 7.59 (t, J=7.8 Hz 1H), 7.83 (dt, J=1.2, 7.8 Hz, 1H), 7.95 (dt, J=1.2, 7.8 Hz, 1H), 8.13-8.20 (m, 3H); $^{13}$C NMR (CD$_3$OD) δ 26.8, 28.9, 37.6, 43.3, 60.5, 64.3, 124.4, 128.8, 129.4, 130.0, 133.4, 135.4, 137.2, 141.4, 146.4, 159.1, 162.3, 171.7; MS (ESI) m/z 312.5 (M+H)$^+$; Anal. (C$_{18}$H$_{19}$ClFN$_3$O.2.5 H$_2$O) C, H, N.

Example 4

Biological Testing/Binding Assays

The Ki values for the inhibition of [3H]epibatidine binding at the α4β2 nAChR in male rat cerebral cortex for compounds are listed in Table A. The binding assays were conducted and the Ki values calculated as described in Carroll, F. I. et al., "Synthesis, nicotinic acetylcholine receptor binding, and antinociceptive properties of 2-exo-2-(2',3'-disubstituted 5'-pyridinyl)-7-azabicyclo[2.2.1]heptanes:epibatidine analogues." J. Med. Chem. 2002, 45, 4755-4761. Compounds (10 mM) were also evaluated for inhibition of binding to α7 nAChR using [$^{125}$I]iodoMLA as previously reported in Carroll et al.

The above compounds were evaluated in two acute pain models, the tail-flick and the hot-plate tests, and the results are listed in Table A (Damaj, M. I. et al., "Antinociceptive and pharmacological effects of metanicotine, a selective nicotinic agonist." J. Pharmacol. Exp. Ther. 1999, 291, 390-398). In the tail-flick method of D'Amour and Smith, (D'Amour, F. E.; Smith, D. L. J. Pharmacol. Exp. Ther. 1941, 72, 74-79), the tail is exposed to a heat lamp and the amount of time taken for the animal to move (flick) its tail away from the heat is recorded. A control response (2-4 s) was determined for each mouse before treatment, and a test latency was determined after drug administration. The method used for the hot-plate test is a modification of those described by Eddy and Leimbach (Eddy, N. B.; Leimbach, D., J. Pharmacol. Exp. Ther. 1953, 107, 385-939) and Atwell and Jacobson (Atwell, L.; Jacobson, A. E., 1978, 7, 42-47). Mice were placed into a 10-cm wide glass cylinder on a hot plate (Thermojust Apparatus) maintained at 55.0° C. Two control latencies at least 10 min apart were determined for each mouse. The normal latency (reaction time) was 8-12 s. The reaction time was scored when the animal jumped or licked its paws. The mice were tested 5 min after subcutaneous (sc) injections of nicotinic ligands for the dose-response determination. Antinociceptive response was calculated as percentage of maximum possible effect (% MPE, where % MPE=[(test−control)/(maximum latency−control)×100]).

To measure the effect of analogs on spontaneous activity, mice were placed into individual Omnitech photocell activity cages (28 cm×16.5 cm) 5 min after sc administration of either 0.9% saline or the epibatidine analog. Interruptions of the photocell beams (two banks of eight cells each) were then recorded for the next 10 min. Data were expressed as number of photocell interruptions. Rectal temperature was measured by a thermistor probe (inserted 24 mm) and digital thermometer (Yellow Springs Instrument Co., Yellow Springs, Ohio).

Readings were taken just before and at different times after the sc injection of either saline or epibatidine analogs. The difference in rectal temperature before and after treatment was calculated for each mouse. The ambient temperature of the laboratory varied from 21 to 24° C. from day to day.

For the antagonist experiments, mice were pretreated sc with either saline or epibatidine analogs 10 min before nicotine. Nicotine was administered at a dose of 2.5 mg/kg, sc (an $ED_{84}$ dose), and mice were tested 5 min later. ED50 and AD50 values with 95% confidence limits were determined.

Table A provides a comparison of epibatidine and varenicline radioligand binding, antinociception and in vitro functional data to 2'-fluoro-3'-(substituted phenyl)deschloroepibatidine analogs. The (−)-epibatidine form was tested with varenicline, and nicotine. The 2'-fluoro-3'-(substituted phenyl)deschloroepibatidine analogs are represented by the formula:

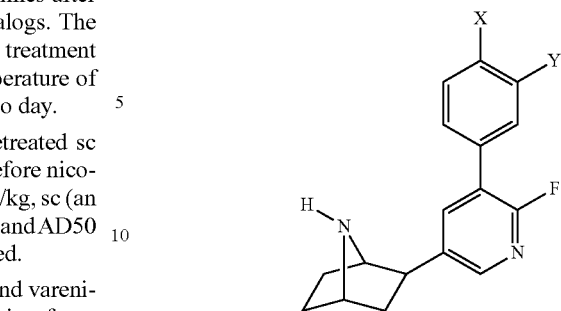

wherein X and Y are identified in the table. Compounds 153, 154, 155, 168, 169, 192 and 193 are represented by formula I above. Compounds 47, 98, 102 and 107 are comparative compounds.

TABLE A

Comparison of epibatidine and varenicline radioligand binding, antinociception and in vitro functional data to 2'-fluoro-3'-(substituted phenyl)deschloroepibatidine analogs

| RTI-7527- | X | Y | αβ [$^3$H] Epibatidine ($K_i$, nM) (Hill slope) | $α_7$ [$^{125}$I]iodo MLA ($K_i$, nM) (Hill slope) | $ED_{50}$ Tail-Flick (mg/kg) | $ED_{50}$ Hot-Plate (mg/kg) | $ED_{50}$ Hypothermia (mg/kg) | $ED_{50}$ Spontaneous Activity (mg/kg) | $AD_{50}$ Tail-Flick (μg/kg) | $AD_{50}$ Hot-Plate (μg/kg) |
|---|---|---|---|---|---|---|---|---|---|---|
| (−)-epibatidine | | | 0.018 ± 0.001 | | 0.006 (0.001-0.01) | 0.004 (0.001-0.008) | 0.004 (0.002-0.008) | 0.001 (0.0005-0.005) | | |
| varenicline | | | 0.12 ± 0.02 | 32.5 ± 1.3 | 11% @ 10 | 10% @ 10 | 2.8 | 2.1 | 0.2 | 470 |
| (±)-47 | H | H | 0.24 ± 0.02 (0.98 ± 0.05) | >2000 | 3% @ 15 | 4% @ 15 | −0.5° C. @ 10 | 4.7 (3.5-8.5) | 500 (250-1500) | 1200 (900-2100) |
| (±)-47 | H | H | 0.24 ± 0.02 (1.13 ± 0.13) | >2000 | 7% @ 15 | 8% @ 15 | −0.4° C. @ 10 | NT | 1000 (500-1500) | 2400 (1900-3800) |
| (−)-47 | H | H | 0.26 ± 0.05 (0.78 ± 0.05) | >2000 | 5% @ 15 | 10% @ 15 | −0.8° C. @ 10 | NT | 80 (30-200) | 700 (100-2500) |
| 98 | H | Cl | 0.073 ± 0.006 (0.78 ± 0.02) | >2000 | 3% @ 10 | 14% @ 10 | 0% @ 10 | 15% @ 10 | 12 (2-60) | 450 (40-1400) |
| 107 | H | $NO_2$ | 0.053 ± 0.004 (1.04 ± 0.004) | >2000 | 3% @ 10 | 20% @ 10 | 0% @ 10 | 6.5 (5.3-8.3) | 0.5 (0.05-0.005) | 130 (50-290) |
| (±)-102 | $NO_2$ | H | 0.009 ± 0.001 (0.68 ± 0.09) | >2000 | 5% @ 10 | 10% @ 10 | 0.21 (0.4-1.9) | 0.22 (0.04-1.2) | 3 (0.8-45) | 120 (10-900) |
| (±)-102 | $NO_2$ | H | 0.021 ± 0.003 | | 4% @ 10 | 5% @ 10 | 2.1 (1.1-3.9) | 1.2 (0.3-5) | 0% @ 10000 | 0% @ 10000 |
| (−)-102 | $NO_2$ | H | 0.022 ± 0.003 | | 10% @ 10 | 22% @ 10 | 2.2 (0.14-33) | 0.57 (0.13-2.3) | 2 (1.2-41) | 180 (30-1200) |
| 153 | $CF_3$ | H | 0.44 ± 0.05 | >2000 | 4% @ 10 | 6% @ 10 | 0% @ 10 | 5% @ 10 | 38 (2-50) | 6000 (4100-8800) |
| (±)-154 | $CH_3SO_2$ | H | 0.17 ± 0.027 | >2000 | 6% @ 10 | 1% @ 10 | 1% @ 10 | 12% @ 10 | 18 (2-160) | 2600 (1100-5800) |
| (±)-154 | $CH_3SO_2$ | H | 0.080 ± 0.008 | | 5% @ 10 | 8% @ 10 | 1.2% @ 10 | 0% @ 5; 70% @ 10 | 82 (22-300) | 40% @ 5000 |
| (−)-154 | $CH_3SO_2$ | H | 0.082 ± 0.007 | | 3% @ 10 | 10% @ 10 | 0% @ 10 | 0% @ 10 | 0.11 (0.03-0.3) | 2760 (878-8642) |

TABLE A-continued

Comparison of epibatidine and varenicline radioligand binding, antinociception and in vitro functional data to 2'-fluoro-3'-(substituted phenyl)deschloroepibatidine analogs

| RTI-7527- | X | Y | αβ [$^3$H] Epibatidine ($K_i$, nM) (Hill slope) | $\alpha_7$ [$^{125}$I]iodo MLA ($K_i$, nM) (Hill slope) | mg/kg | | | | $AD_{50}$ (μg/kg) | |
|---|---|---|---|---|---|---|---|---|---|---|
| | | | | | $ED_{50}$ Tail-Flick | $ED_{50}$ Hot-Plate | $ED_{50}$ Hypothermia | $ED_{50}$ Spontaneous Activity | Tail-Flick | Hot-Plate |
| 155 | CN | H | 0.19 ± 0.012 | >2000 | 4% @ 10 | 18% @ 10 | 0% @ 10 | 0% @ 10 | 6 (3-100) | 24% @ 10000 |
| 169 | H | CONH$_2$ | 0.36 ± 0.088 | 870 ± 150 | 5.6 (3.8-8.2) | 3.6 (1-2.9) | 1.7 (1-2.9) | 1 (0.3-2.9) | 10% @ 500 | 20% @ 500 |
| 168 | CONH$_2$ | H | 0.12 ± 0.021 | 1870 ± 150 | 16% @ 10 | 60% @ 10 | 4.2 (1.5-11.6) | 3.5 (1-11.3) | 9 (3-31) | 1% @ 2000 |
| 192 | CF$_3$SO$_2$ | H | 0.03 ± 0.004 | >2000 | 3% @ 10 | 15% @ 10 | 0% @ 10 | 4.2 (1-16) | 1600 (1500-1800) | 50% @ 10000 |
| 193 | H$_2$NSO$_2$ | H | 0.94 ± 0.061 | >2000 | 4% @ 10 | 19% @ 10 | 0% @ 10 | 5% @ 10 | 0.9 (0.4-1.8) | 10 (1-180) |

Example 5

RTI-102, RTI-154, varenicline and α-conotoxin AUIB, a selective $\alpha_3\beta_4$ antagonist of peptidergic nature were evaluated in nicotine conditioned place preference (CPP) tests. CPP was used to measure both reward and aversion and determine if compounds that possess inhibition properties on $\alpha_4\beta_2$ nAChR subtypes will block nicotine reward.

CPP was performed using a three-chamber place-conditioning apparatus (Med Associates). The center compartment is grey while the two test chambers are either black or white with differing floor materials.

On day 1, mice (n=8/treatment group) were introduced into the CPP chamber and their baseline preference for each chamber measured for 15 min. On day 2, mice were given the test compound or vehicle s.c. 10 min prior to either vehicle or nicotine (0.5 mg/kg) for each conditioning session. Immediately following injection, mice were randomly placed in either of the two test compartments for 30 min. Five hours later testing was repeated following another injection of saline or nicotine. Mice will be counter-balanced in terms of which side is paired with drug and order of treatment (saline vs. nicotine at first injection). Control mice received saline at both injections while nicotine-treated mice received one saline injection paired with one chamber and nicotine injection with the other. This procedure was repeated for a total of 3 conditioning days (days 3-4), giving a total of 3 nicotine and 3 saline conditioning trials. On day 5, mice were placed in the center compartment and preference for either test compartment tested for 15 min. Preference for the drug-paired chamber was expressed as time spent on that side on the test day (day 5) minus the time spent in that chamber on the preconditioning day (day 1). Treatment groups include 1) vehicle+saline/nicotine (0.5 mg/kg), 2) analog (minimum 3 doses)+saline/nicotine, 3) analog (at highest inactive dose that blocks nicotine)+saline/saline, and 4) vehicle+saline/saline. Male ICR adult mice were conditioned with saline or nicotine (0.5 mg/kg) subcutaneously (s.c.) for three days and preference scores were calculated.

RTI-102 dose-dependently blocked nicotine CPP in the mouse. In addition, RTI-154 at a dose of 0.5 mg/kg, totally blocked the development of nicotine-induced CPP. RTI-154 and RTI-102 did not induce significant preference or aversion by themselves at the doses used. No impact on the locomotor activity of animals was seen with these compounds at the tested doses. Furthermore, varenicline dose-dependently blocked nicotine CPP in the mouse without a significant effect on its own Finally, we tested the effects of the selective $\alpha_3\beta_4$ antagonist compound, α-conotoxin AUIB, after i.c.v. injection and it blocked the development of nicotine reward in the CPP test.

Example 6

The cardiovascular effects of the nicotinic full agonists nicotine and epibatidine, as well as the partial agonist varenicline were evaluated. The immediate effects of saline and other injections are due to an autonomic response to the injection procedure. Each of these drugs produced substantial increases in blood pressure. Dihydro-beta-erythroidine (DHβE) alone produced no changes in blood pressure. RTI-102 and RTI-154 were also tested.

Male Sprague-Dawley rats (approximately 300 g) were obtained from Harlan, Inc. (Indianapolis, Ind.) and group-housed upon arrival. Food and water were freely available for all rats at all times. Housing and experimental rooms were maintained on a 12 h light/dark cycle with lights on at 7:00 AM with an average temperature of 21° C.

Surgical Procedures. To measure changes in heart rate and mean arterial pressure, rats were implanted with telemetric transmitters (TA11PAC40 or TL11M2-C50-PXT, Data Sciences International, Transoma Medical Inc., St. Paul, Minn., USA) under ketamine (90 mg/kg, i.p.) and xylazine (10 mg/kg, i.p.) anesthesia. An incision is made in the skin approximately 1 in to the left or right of the spine and over the left or right thigh to expose the femoral artery. The transmitter is placed into the incision on the dorsal side and into a subcutaneous pocket (made by separating the connective tissue between the skin and muscle) on the side of the abdomen. This positioning prevents the rats from manipulating the incision site and gaining access to the transmitter. The catheter extending from the base of the transmitter is threaded subcutaneously, placed 3 cm into the femoral artery, and secured with suture. Incisions were closed with 5.0 Ethicon nylon monofilament suture. Following surgery, rats were singly-housed and monitored for at least 7 days for signs of recovery (normal eating, drinking, and defecating patterns) prior to experimentation. All rats continued to have free access to food and water at all times.

Telemetry System. The system consists of battery-operated transmitters surgically implanted (described above), Physiotel® receivers, the DSI Data Exchange Matrix, and the Dataquest A.R.T. system, which collects and stores digital data from the receiver onto a computer (Data Sciences International, Transoma Medical Inc., St. Paul, Minn., USA). Blood pressure and heart rate data were analyzed by the Dataquest A.R.T. Gold Analysis 3.01 software.

At the start of an experiment, rats' home cages were placed on top of the receivers, and baseline data was collected for at least 1 h to allow heart rate and blood pressure to return to resting levels. All rats were given a saline injection to ensure that they are habituated to the injection and handling procedure on the test day. After heart rate and blood pressure returned to resting levels again, rats were injected with a treatment, consisting either of a single drug dose or a pretreatment drug administered 15 min prior to a test drug. Data was collected for at least 2 h following the last injection. All injections were administered subcutaneously (s.c.) in a volume of 1 ml/kg.

Each rat was used to evaluate multiple experimental conditions, such that each rat may receive as many as 4-6 different treatments, one per week with at least 6 days between drug exposures. Our extensive preliminary experiments demonstrated that this procedure was sufficient to prevent the development of tolerance or sensitization to the effects of nicotine and to prevent changes in resting heart rate and blood pressure levels over the course of 6 weeks. Once the rats weigh approximately 450 g (body weight at time of transmitter implant: 300-350 g), the rat is no longer used for experiments, and the transmitter is removed.

Data were collected throughout baseline, before, and after drug treatments. The analysis program calculated an average heart rate and mean arterial pressure (MAP) every 10 sec. These 10 secepochs are then averaged over 1 min per rat, and data from at least 6 rats were averaged for each treatment group.

FIG. 1, left panel, shows the cardiovascular effects of nicotine, epibatidine and varenicline compared to saline. Heart rate and mean arterial pressure is graphically shown versus time for the comparative compounds indicated. FIG. 1, right panel, graphically shows the cardiovascular effects of RTI-154, and comparative compounds RTI-98, RTI-102 and dihydro-beta-erythroidine (DHβE) compared to saline. These compounds are represented as follows:

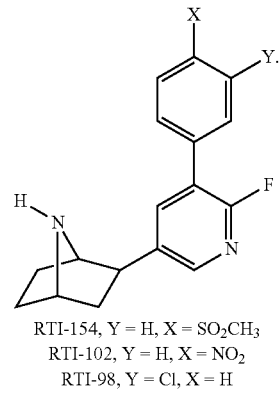

RTI-154, Y = H, X = SO$_2$CH$_3$
RTI-102, Y = H, X = NO$_2$
RTI-98, Y = Cl, X = H

Figure 2:
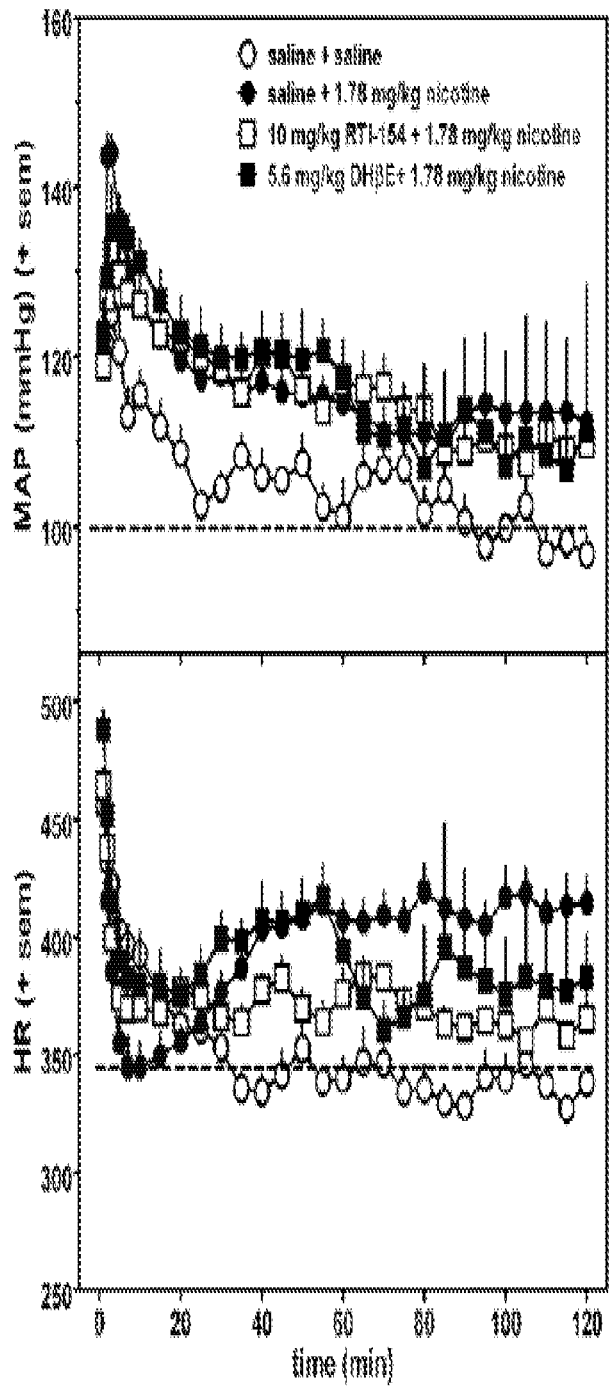
FIG. 2 is a graphical representation of cardiovascular effects mean arterial pressure and heart rate observed over time in rats after administration of saline, saline plus 1.78 mg/kg nicotine, 10 mg/kg of RTI-154 plus 1.78 mg/kg nicotine and 5.6 mg/kg of dihydro-beta-erythroidine (DHβE) plus 1.78 mg/kg nicotine.

Both RTI-98 and RTI-102 had minimal effects on heart rate, but produced sustained increases in blood pressure. RTI-154, like DHβE, had no cardiovascular effects. Without being bound by any theory, it may be that RTI-98 and RTI-102 are agonists at a nAChR that mediates the cardiovascular effects of nicotine. RTI-154's cardiovascular effects, on the other hand, were identical to those of DHβE, indicating that these two drugs do not appear to interact with the nACh receptors that mediate cardiovascular effects of nicotine. As graphically shown in FIG. 2, when RTI-154 or DHβE was given prior to nicotine in the cardiovascular assay, it did not block nicotine's hypertensive effects, suggesting that RTI-154 does not bind to the peripheral receptors that modulate acetylcholine's cardiovascular effects. This is a positive outcome since it indicates a selective action at central nACh receptors.

Example 7

A drug discrimination assay was performed to measure the relevant effects of nicotine as it influences tobacco use and abuse. In a drug discrimination assay, food restricted rates are trained to make one response (select one of two nose-poke apertures in the test chamber) following administration of a particular drug, and a different response (select the other aperture) following administration of saline. The appropriate response is followed by delivery of food, and there is no cue as to which aperture will result in food delivery other than the presence or absence of the drug. Once trained, the animals respond on the "drug-associated" aperture following drug administration and on the "saline-associated" aperture following saline administration. In addition, administration of drug doses that are smaller than the training dose produce intermediate responses on the drug-associated aperture such that monotonically increasing dose-response curves can be generated in drug discrimination assays. The shape of the curve that results when the various doses of the training drug are given following a putative antagonist may be interpreted such that parallel rightward shifts in the dose response curves indicate competitive antagonism, whereas rightward and downward shifts suggest non-competitive antagonism.

Male Sprague-Dawley rats were obtained from Harlan, Inc (Indianapolis, Ind.) and singly housed in polycarbonate cages with water continuously available. All rats weighed approximately 280-290 gms at the start of the experiment. A food-restricted diet of Purina rodent food allowed the animals to grow but maintain motivation to respond to earn food pellets. A 12 hr light-dark cycle turned the lights on at 7:00 am. Standard operant conditioning chambers (ENV-008, Med-Associates, St Albans, Vt.) were used for establishing and evaluating the nicotine discrimination. Each chamber contains two nose-poke devices with apertures containing yellow LED lights on either side of a dipper capable of delivering 50 µl of fluid into a third opening.

Initially, each rat was trained to insert its nose into one of the apertures and received vanilla-flavored Ensure as a consequence. During discrimination training, rats designated in the small dose group were injected with either saline or 0.32 mg/kg of nicotine. Ten consecutive responses on the appropriate lever (one side following saline administration; the other side following nicotine administration) was followed by presentation of the Ensure for 10 s, followed by a 10 s timeout. Selection of the incorrect lever, and completion of the 10 consecutive responses in this lever results in a 10 s timeout. Criteria for learning the discrimination are 1) responding on the first FR of the session is completed on the injection appropriate aperture; 2) >85% of the total session responses are made on the injection-appropriate aperture.

Each session was divided into several components of 25 min duration. Following an injection, the first five minutes of each component were black out, and the stimulus lights were illuminated for the remaining 20 min, during which injection-appropriate responses were reinforced. The 20 min $S^d$ period is gradually reduced to 5 min after the nicotine discrimination has been established so that conditions become 5 min black out and 5 min $S^d$ period.

One to four components comprised daily sessions Animals were injected with saline or nicotine prior to the start of the session, or following one or more of the 10 min components. Possible injection conditions were (S=saline, N=nicotine) S—S—S—S; N; S—N; S—S—N; S—S—S—N. Nicotine administration is always given in the final component if it is given at all.

If a potential antagonist was given, it was administered prior to the session at a time determined by earlier studies to be sufficient for peak effects to be established. The session components then comprised increasing doses of nicotine, each given before consecutive blackout periods. No more than two antagonist sessions were given each week, and once each month a nicotine dose-response curve was determined to assure no changes in sensitivity to nicotine. Full generalization to the nicotine discriminative cue is defined by >85% responding on the drug-associated aperture and completing at least one FR.

A second, large-nicotine trained group of rats were treated in an identical manner except that their training dose of nicotine is 1.78 mg/kg.

Data analysis: Rates of responding are calculated as the number of responses that occur during the presentation of the 5 min $S^d$ periods that indicate reinforcer availability. Responses on either manipulandum contribute to this measure. Discrimination outcomes are expressed as the percent of responses occurring on the nicotine-associated aperture out of the total number of responses on both the drug- and saline-associated apertures. Data were averaged across 5-6 rats in each dose condition. Changes in agonist potency in the presence of antagonists was measured by determining ED50 values using GraphPad Prism 6 Software (San Diego, Calif.). These were calculated for each rat from a straight line analysis of % drug-appropriate responding, including one dose that produces <10%, and one dose that produces >90% drug-appropriate responding.

In this study, two groups of rats were trained to discriminate either a small dose of nicotine or a large dose of nicotine from saline. The primary conclusion from this study that examined the discriminative stimulus effects and antagonist effects of partial nicotine agonists and several nicotine antagonists, was that the small dose of nicotine appears to produce its discriminative stimulus effects through a DHβE-sensitive site, which we presume to be the $\alpha_4\beta_2$ nAChR.

Figure 3:
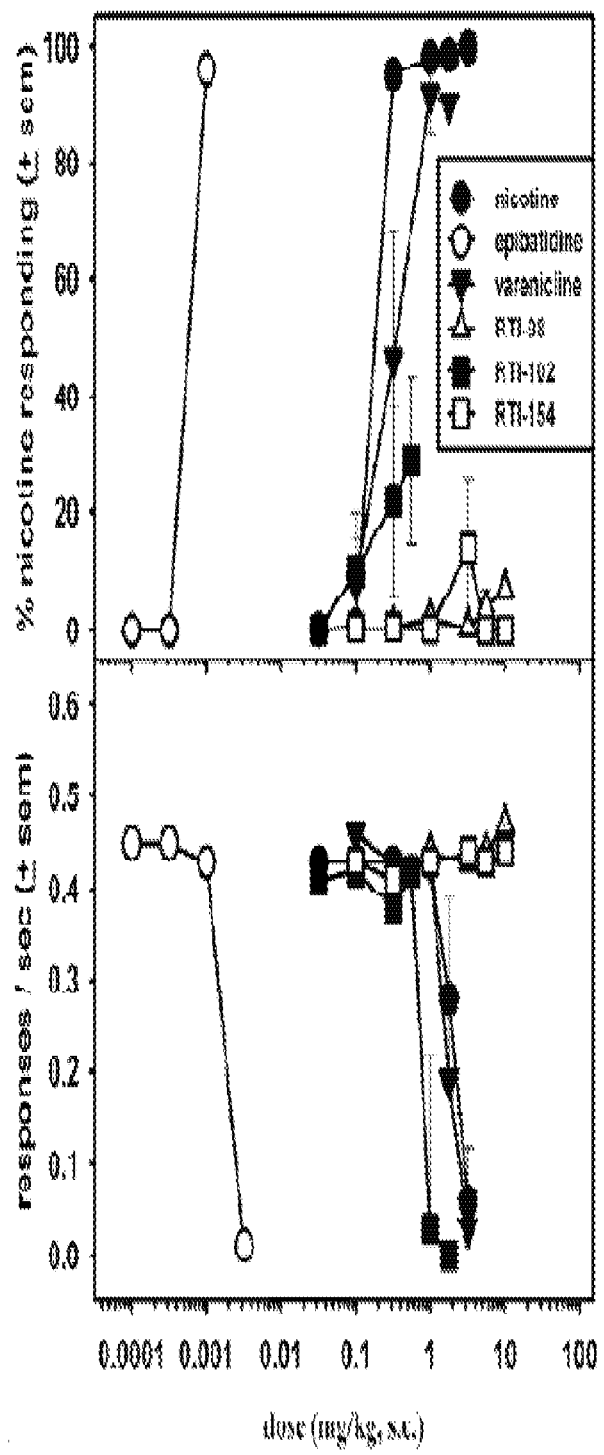
FIG. 3 is a graphical representation of the dose-responsive discriminative stimulus effects of nicotine, epibatidine, varenicline, comparative compounds RTI-98 and RTI-102 and a compound according to the present disclosure, RTI-154.

Evaluation of the discriminative stimulus effects of a variety of nAChR ligands (FIG. 3) indicated that epibatidine is an extremely potent full nicotine-like agonist. As graphically shown in FIG. 3, varenicline also produced nearly full nicotine-like discriminative stimulus effects, suggesting that it is a fairly high efficacy partial agonist. (It should be noted that the discriminative stimulus assay is quite sensitive to agonist effects.) RTI-102 suppressed rates of responding at doses that produced around 30% nicotine-appropriate responding, demonstrating efficacy that is less than that of varenicline. Neither RTI-98 nor RTI-154 produce any nicotine-appropriate responding and did not suppress ongoing rates of responding. These compounds therefore had no efficacy at the nicotine receptors that underlie the discriminative stimulus effects of small doses of nicotine. These drugs do, however, bind to the nicotine receptor.

Figure 4:
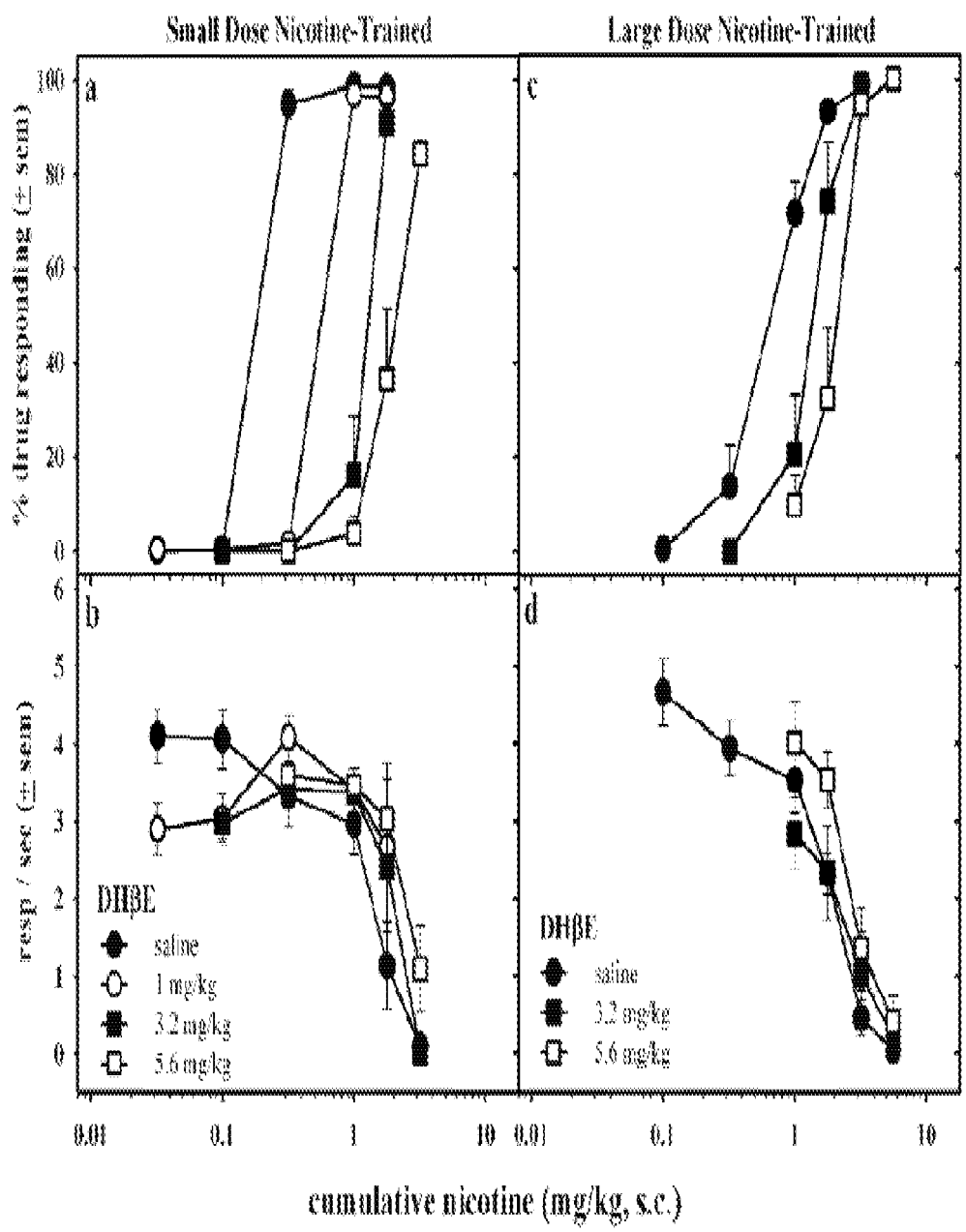
FIG. 4 is a graphical representation of the dose-responsive discriminative stimulus effects of nicotine (0.3 and 1.8 mg/kg) and varying doses of dihydro-beta-erythroidine (DHβE).

As graphically shown in FIG. 4 (top left panel), DHβE produced parallel rightward shifts in the small-dose nicotine dose-effect curve. DHβE affinity for the $\alpha_4\beta_2$ receptor supports the notion that this receptor is responsible for the discriminative stimulus effects of the small dose of nicotine.

The larger dose of nicotine apparently also acts on this receptor, but recruits additional nicotine receptors as evidenced by the fact that DHβE produced much less robust rightward shifts in the large dose-nicotine dose-response curve (FIG. 4, top right panel). The rate-decreasing effects of both doses of nicotine appear to be mediated by a receptor in addition to or other than the $\alpha_4\beta_2$ receptor, since DHβE did not antagonize these effects of nicotine (FIG. 4, bottom panels).

Figure 5:
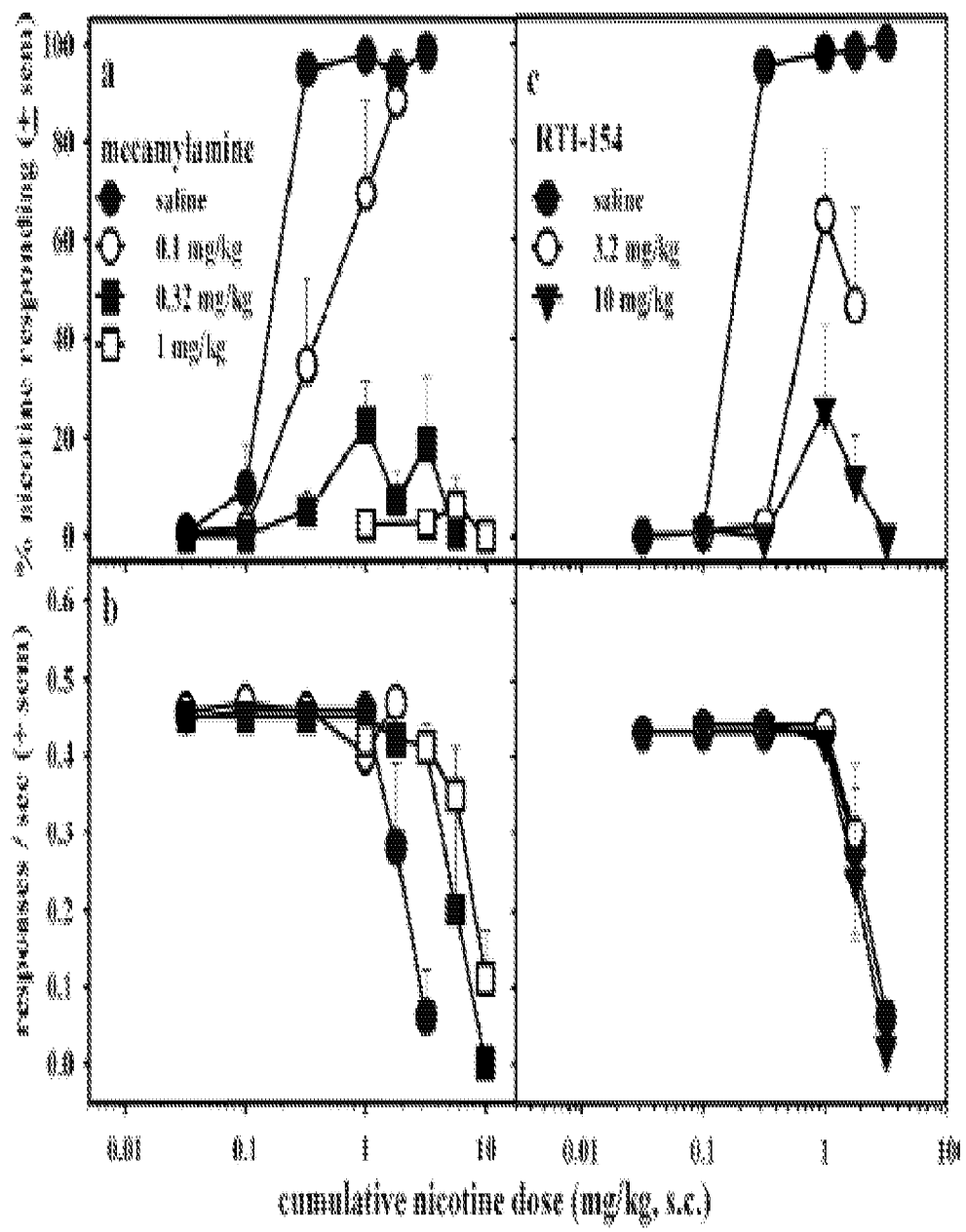
FIG. 5 is a graphical representation of the dose-responsive discriminative stimulus effects of nicotine (0.3 mg/kg) and varying doses of mecamylamine compared to varying doses of a compound according to the present disclosure, RTI-154.

Mecamylamine, which binds in a nonselective and non-competitive manner to nicotine receptors, produced a rightward and downward shift in the discriminative stimulus effects of small doses of nicotine (FIG. 5 top, left panel), and a parallel rightward shift in the rate-decreasing effects of these doses of nicotine (FIG. 5, bottom, left panel). RTI-154 also produced rightward and downward shifts in the discriminative stimulus effects of a small dose of nicotine (FIG. 5, top right), suggesting a possible non-competitive interaction of this compound with the $\alpha_4\beta_2$ receptor. RTI-154 did not, however, alter the potency of nicotine in suppressing ongoing rates of responding (FIG. 5, bottom right), so it is not acting in as non-selective manner as is mecamylamine.

Without being bound to any theory, it is believed that drugs that block the discriminative stimulus effects of a small training dose of nicotine, but are less able to modify the discriminative stimulus effects of a large training dose of nicotine and do not antagonize the rate-decreasing effects of nicotine in these assays, are likely to be acting selectively on the α4β2 receptor, which is believed to be responsible for mediating both the discriminative stimulus and the reinforcing stimulus of nicotine.

While the disclosure has been has been set out herein in reference to specific aspects, features and illustrative embodiments, it will be appreciated that the utility of the disclosure is not thus limited, but rather extends to and encompasses numerous other variations, modifications and alternative embodiments, as will suggest themselves to those of ordinary skill in the field of the present disclosure, based on the description herein. Correspondingly, the invention as hereinafter claimed is intended to be broadly construed and interpreted, as including all such variations, modifications and alternative embodiments, within its spirit and scope.

What is claimed is:

1. A compound represented by formula (I)

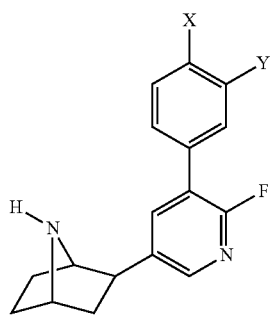

(I)

wherein X is H and Y is —SO$_2$CH$_3$, —SO$_2$NH$_2$, or —SO$_2$CF$_3$; or X is —SO$_2$CH$_3$, —SO$_2$NH$_2$, or —SO$_2$CF$_3$, and Y is H; or a pharmaceutically acceptable salt thereof.

2. The compound of claim 1, wherein X is H and Y is —SO$_2$CH$_3$, —SO$_2$NH$_2$, or —SO$_2$CF$_3$, or a pharmaceutically acceptable salt thereof.

3. The compound of claim 1, wherein X is —SO$_2$CH$_3$, —SO$_2$NH$_2$, or —SO$_2$CF$_3$, and Y is H, or a pharmaceutically acceptable salt thereof.

4. The compound of claim 1, wherein X is —SO$_2$CH$_3$ and Y is H, or a pharmaceutically acceptable salt thereof.

5. The compound of claim 1, wherein X is —SO$_2$NH$_2$ and Y is H, or a pharmaceutically acceptable salt thereof.

6. The compound of claim 1, wherein X is —SO$_2$CF$_3$ and Y is H, or a pharmaceutically acceptable salt thereof.

7. A composition comprising a compound according to claim 1 and a pharmaceutically acceptable carrier.

8. A method of treating nicotine addiction, comprising administering an effective amount of a composition of claim 7 to a subject in need thereof.

9. A method for selectively modulating the function of a nicotinic acetylcholine receptor comprising administering to a subject in need thereof an effective amount of a composition of claim 7.

10. The method of claim 9, wherein the selective modulation comprises inactivation of the function of one or more nicotinic acetylcholine receptor subtype as an antagonist.

11. A method for treating a subject having a condition or disorder selected from smoking addiction, nicotine addiction, or pain, the method comprising administering to said subject having or susceptible to said condition or disorder an effective amount of a compound represented by formula (I)

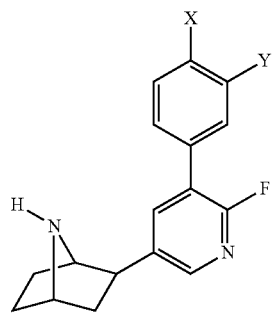

(I)

wherein X is H and Y is —SO$_2$CH$_3$, —SO$_2$NH$_2$, or —SO$_2$CF$_3$; or X is —SO$_2$CH$_3$, —SO$_2$NH$_2$, or —SO$_2$CF$_3$, and Y is H; or a pharmaceutically acceptable salt thereof.

12. The method of claim 11, wherein X is H and Y is —SO$_2$CH$_3$, —SO$_2$NH$_2$, or —SO$_2$CF$_3$, or a pharmaceutically acceptable salt thereof.

13. The method of claim 11, wherein X is —SO$_2$CH$_3$, —SO$_2$NH$_2$, or —SO$_2$CF$_3$, and Y is H, or a pharmaceutically acceptable salt thereof.

14. The method of claim 11, wherein X is —SO$_2$CH$_3$ and Y is H, or a pharmaceutically acceptable salt thereof.

15. The method of claim 11, wherein X is —SO$_2$NH$_2$ and Y is H, or a pharmaceutically acceptable salt thereof.

16. The method of claim 11, wherein X is —SO$_2$CF$_3$ and Y is H, or a pharmaceutically acceptable salt thereof.

17. The compound of claim 1, wherein Y is —SO$_2$CH$_3$ and X is H, or a pharmaceutically acceptable salt thereof.

18. The compound of claim 1, wherein Y is —SO$_2$NH$_2$ and X is H, or a pharmaceutically acceptable salt thereof.

19. The compound of claim 1, wherein Y is —SO$_2$CF$_3$ and X is H, or a pharmaceutically acceptable salt thereof.

20. The method of claim 11, wherein Y is —SO$_2$CH$_3$ and X is H, or a pharmaceutically acceptable salt thereof.

* * * * *

UNITED STATES PATENT AND TRADEMARK OFFICE
CERTIFICATE OF CORRECTION

| | | |
|---|---|---|
| PATENT NO. | : 9,150,581 B2 | Page 1 of 1 |
| APPLICATION NO. | : 14/368111 | |
| DATED | : October 6, 2015 | |
| INVENTOR(S) | : Frank Ivy Carroll et al. | |

It is certified that error appears in the above-identified patent and that said Letters Patent is hereby corrected as shown below:

IN THE SPECIFICATION

Column 24, line 25: "11.40. Found:" should be -- 11.40; found: --.

Signed and Sealed this
Eighth Day of December, 2015

Michelle K. Lee
*Director of the United States Patent and Trademark Office*